United States Patent
Messing et al.

(10) Patent No.: US 9,603,317 B2
(45) Date of Patent: Mar. 28, 2017

(54) COMPOSITIONS AND METHODS FOR RAPID AND EFFICIENT PRODUCTION OF QUALITY PROTEIN MAIZE

(75) Inventors: Joachim Messing, Somerset, NJ (US); Yongrul Wu, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 726 days.

(21) Appl. No.: 13/362,641

(22) Filed: Jan. 31, 2012

(65) Prior Publication Data
US 2012/0198583 A1 Aug. 2, 2012

Related U.S. Application Data

(60) Provisional application No. 61/438,206, filed on Jan. 31, 2011.

(51) Int. Cl.
| | |
|---|---|
| *A01H 1/02* | (2006.01) |
| *A01H 5/00* | (2006.01) |
| *A01H 5/10* | (2006.01) |
| *C07K 14/415* | (2006.01) |
| *C07K 14/425* | (2006.01) |
| *C12N 15/82* | (2006.01) |

(52) U.S. Cl.
CPC .............. *A01H 1/02* (2013.01); *A01H 5/10* (2013.01); *C07K 14/415* (2013.01); *C07K 14/425* (2013.01); *C12N 15/8218* (2013.01); *C12N 15/8251* (2013.01)

(58) Field of Classification Search
CPC ....................................................... A01H 1/02
USPC ........................................................ 800/275
See application file for complete search history.

(56) References Cited

U.S. PATENT DOCUMENTS

| | | | | |
|---|---|---|---|---|
| 2008/0078003 | A1* | 3/2008 | Zuo-Yu et al. | 800/275 |
| 2009/0246350 | A1* | 10/2009 | Malvar et al. | 426/629 |

OTHER PUBLICATIONS

Moose et al. 2004, Trends in Plant Science 9:358-364.*
Esen, A. et al., A proposed nomenclature for the alcohol-soluble proteins (zeins) of maize (*Zeamays* L.), J Cereal Sci., 1987, 117-128, 5.
Woo, YM et al., Genomics analysis of genes expressed in maize endosperm identifies novel seed proteins and clarifies patterns of zein gene expression. Plant Cell., 2001, 2297-2317, 13.
Larkins, BA et al., Synthesis and deposition of zein in protein bodies of maize endosperm, Plant Physiol, 1978, 256-263, 62.
Lending CR et al., Changes in the zein composition of protein bodies during maize endosperm development, Plant Cell., 1989, 1011-1023, 1.
Wu Y et al., RNA interference-mediated change in protein body morphology and seed opacity through loss of different zein proteins, Plant Physiol, 2010, 337-347, 153.
Kim CS et al., A defective signal peptide in a 19-kD alpha-zein protein causes the unfolded protein response and an opaque endosperm phenotype in the maize De*-B30 mutant, Plant Physiol, 2004, 380-387, 134.
Coleman CE et al, A defective signal peptide in the maize high-lysine mutant floury 2, PNAS USA. 1995, 6828-6831, 92.

(Continued)

*Primary Examiner* — Li Zheng
(74) *Attorney, Agent, or Firm* — Kathleen D. Rigaut; Dann, Dorfman, Herrell and Skillman

(57) ABSTRACT

Compositions and methods for the universal and accelerated production of QPM are disclosed.

9 Claims, 21 Drawing Sheets

(56) References Cited

OTHER PUBLICATIONS

Mertz ET et al., Mutant gene that changes protein composition and increases lysine content of maize endosperm, Science, 1964, 279-280, 145.
Segal G et al., A new opaque variant of maize by a single dominant RNA•interference-inducing transgene. Genetics, 2003, 387-397, 165.
Geetha KB et al., Opaque-2 modifiers increase gamma-zein synthesis and alter its spatial distribution in maize endosperm, 1991, Plant Cell, 1207-1219, 3.
Schmidt RJ et al., Opaque-2 is a transcriptional activator that recognizes a specific target site in 22-kD zein genes, Plant Cell, 1992, 689-700, 4.
Hunter et al. Maize opaque endosperm mutations create extensive changes in patterns of gene expression. Plant Cell., 2002, 2591-612, 14(10).
Gibbon BC et al., Altered starch structure is associated with endosperm modification in Quality Protein Maize, PNAS USA, 2003, 15329-15334, 100.
Bass HW et al., A maize ribosome-inactivating protein is controlled by the transcriptional activator Opaque-2, Plant Cell, 1992, 225-234, 4.
Huang S et al., Improving nutritional quality of maize proteins by expressing sense and antisense zein genes, J Agric Food Chem., 2004; 1958-1964, 52.
Moose et al., Maize selection passes the century mark: a unique resource for 21st century genomics, Trends Plant Sci., 2004, 358-64, 9(7).
Sodek et al., Amino acid composition of proteins isolated from normal, opaque-2, and floury-2 com endosperms by a modified Osborne procedure, J Agric Food Chem., 1971, 1144-1150, 19.
Xu et al. Organization of the prolamin gene family provides insight into the evolution of the maize genome and gene duplications in grass species, Proc Nat. Acad. Sci USA., 2008, 14330-14335, 105.
Holding et al. The Maize Flouryl Gene Encodes a Novel Endoplasmic Reticulum Protein Involved in Zein Protein Body Formation, Plant Cell., 2007, 2569-2582, 19.
Coleman et al. Expression of a mutant α-zein creates the floury2 phenotype in transgenic maize, Proc Natl Acad Sci USA, 1997, 7094-7097, 94(13).
Kim et al. The maize Mucronate mutation is a deletion in the 16-kDa gamma-zein gene that induces the unfolded protein response. Plant J., 2006, 440-51, 48(3).

Osborne et al. Nutrative properties of proteins of the maize kernel. J Biol Chem., 1914, 1-16, 18(1).
Osborne et al. Amino-acids in nutrition and growth. J Biol Chem., 1914, 325-349, 17.
Emerson et al. A summary of linkage studies in maize. Cornell University Agricultural Experiment Station Memoir, 1935, 1-83, 180.
Prasanna, Quality protein maize, Current Science, 2001, 1308-1319, 81(10).
Tesso et al. Sorghum protein digestibility is affected by dosage of mutant alleles in endosperm cells. Plant Breeding, 2008, 579-586, 127.
Ueda et al. Mutations of the 22- and 27-kD zein promoters affect transactivation by the Opaque-2 protein. Plant Cell., 1992, 701-9, 4(6).
Holding et al. Genetic analysis of opaque2 modifier loci in quality protein maize. Theor Appl Genet., 2008, 157-170, 117.
Dannenhoffer et al. Opaque-15, a maize mutation with properties of a defective opaque-2 modifier. Proc Natl Acad Sci USA, 1995, 1931-193, 92(6).
Oria et al. A highly digestible sorghum mutant cultivar exhibits a unique folded structure of endosperm protein bodies. Proc Natl AcadSci USA, 2000, 5065-5070, 97.
Lawton et al., Isolation of Zein Using 100% Ethanol, Cereal Chem., 2006, 565-568, 83(5).
Or et al. Opaque2 modifiers act post-transcriptionally and in a polar manner on gamma-zein gene expression in maize endosperm. Plant Cell., 1993, 1599-609, 5(11).
Wu et al. Non-Mendelian regulation and allelic variation of methionine-rich delta-zein genes in maize. Theoretical and Applied Genetics, 2009, 721-731, 119(4).
Wang et al. Quantitative trait locus mapping of loci influencing elongation factor 1 alpha content in maize endosperm. Plant Physiol., 2001, 1271-82, 125.
Wolf et al. Subcellular structure of endosperm protein in high-lysine and normal corn. Science, 1967, 556-7, 157 (3788).
Bass et al., Zein synthesis in maize endosperm by polyribosomes attached to protein bodies, Proc. Nat. Acad. Sci. USA, 1976, 515-519, 73(2).
Burr et al. Zein synthesis in maize endosperm by polyribosomes attached to protein bodies. Proc Natl Acad Sci USA, 1976, 515-519, 73(2).
Duvick et al. Protein Granules of Maize Endosperm Cells. Cereal Chem., 1961, 374-385, 38.
Clore et al. EF-1[alpha] Is Associated with a Cytoskeletal Network Surrounding Protein Bodies in Maize Endosperm Cells. Plant Cell., 1996, 2003-2014, 8(11).

\* cited by examiner

1, B73; 2, IHP; 3, IRHP; 4, ILP; 5, IRLP

SEQUENCE LISTING

```
<160> NUMBER OF SEQ ID NOS: 29

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ccagaattcc tttataatca acccgcactc                                      30

<210> SEQ ID NO 2
<211> LENGTH: 30
<212> TYPE: DNA
<213> ORGANISM: Artificial Sequence
<220> FEATURE:
<223> OTHER INFORMATION: Primer
```

```
<400> SEQUENCE: 2
aatcccggga ccatggtgtc gatcgggttc                                    30

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
attcccgggt cagtagtagg gcggaatg                                      28

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
atatccggat gaagatggtc atcgttc                                       27

<210> SEQ ID NO 5
<211> LENGTH: 28
<212> TYPE: DNA
<213> ORGANISM: Artificial Sequence
<220> FEATURE:
<223> OTHER INFORMATION: Primer

<400> SEQUENCE: 5
attagatcta tgaagatggt catcgttc                                      28

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
aattctagat cagtagtagg gcggaatg                                      28

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
attcccggga ctcaactagc tagctagcc                                     29

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
atatccggat gagggtgttg ctcgttgc                                      28

<210> SEQ ID NO 9
```

```
<211> LENGTH: 29
<212> TYPE: DNA
<213> ORGANISM: Artificial Sequence
<220> FEATURE:
<223> OTHER INFORMATION: Primer

<400> SEQUENCE: 9
attagatcta tgagggtgtt gctcgttgc                                      29

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
aattctagaa ctcaactagc tagctagcc                                      29

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
atatccggat ggatccatgg tgagcaaggg cgag                                34

<210> SEQ ID NO 12
<211> LENGTH: 35
<212> TYPE: DNA
<213> ORGANISM: Artificial Sequence
<220> FEATURE:
<223> OTHER INFORMATION: Primer

<400> SEQUENCE: 12
attagatctt gagctcttac ttgtacagct cgtcc                               35

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
atatctagaa ctgcagcggc gcaaaaatca ccagtc                              36

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
attaagcttt gcaggtcact ggattttgg                                      29

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
```

```
acaaccacta cctgagcac                                              19

<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
gttcgacatg gtacgtcag                                              19

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
attggagcca gtgctactg                                              19

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tgggtggact ctaccagtac                                             20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
atggatagag gagatttccc                                             20

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
agcctcatcc ccagccac                                               18

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
aggttccctg cagctggc                                               18

<210> SEQ ID NO 22
<211> LENGTH: 19
<212> TYPE: DNA
```

```
<213> ORGANISM: Artificial Sequence
<220> FEATURE:
<223> OTHER INFORMATION: Primer

<400> SEQUENCE: 22 atacccact caaccaccg                                                    19

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
gcaggatccg aactgctg                                                    18

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
gcaatcttga cagcagcac                                                   19

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
tgtcattgct gctgcatgg                                                   19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tttgcgctcc tagctctttg                                                  20

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
tatctagaat gcagcaccaa c                                                21

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
acaaccacta cctgagcac                                                   19
```

```
<210> SEQ ID NO 29
<211> LENGTH: 29
<212> TYPE: DNA
<213> ORGANISM: Artificial Sequence
<220> FEATURE:
<223> OTHER INFORMATION: Primer

<400> SEQUENCE: 29
attaagcttt gcaggtcact ggattttgg                                              29
```

COMPOSITIONS AND METHODS FOR RAPID AND EFFICIENT PRODUCTION OF QUALITY PROTEIN MAIZE

This application claims priority to U.S. Provisional Application No. 61/438,206, filed Jan. 31, 2011, which is incorporated by reference herein as though set forth in full.

FIELD OF THE INVENTION

The present invention relates to the fields of plant genetic engineering and nutrition. More specifically, the present invention provides compositions and methods useful for accelerated production of quality protein maize at reasonable cost.

BACKGROUND OF THE INVENTION

Several publications and patent documents are cited throughout the specification in order to describe the state of the art to which this invention pertains. Each of these citations is incorporated herein by reference as though set forth in full.

In order to enhance their nutritional value, seed crops have been targets of genetic engineering efforts to either produce valuable proteins or alter the amino acid composition of existing proteins (Rademacher et al., 2009). However, what is frequently ignored is the subcellular function that proteins play in the development of the seed. In maize (*Zea mays*), the endosperm storage proteins constitute a major protein component in the seed. Most of them belong to the prolamins, common in many grass species, and in maize are referred to as zeins. The alcohol-soluble zein fraction extracted by the Osborne method without reducing agent is called zein-1 and consists mainly of the 19-1W (z1A, z1B, and z1D) and 22-1W (z1C)-zeins (Song and Messing, 2003). The fraction of alcohol-soluble proteins extracted with a disulfide reducing agent (Moureaux and Landry, 1968; Paulis et al., 1969; Landry and Moureaux, 1970) is called zein-2 (Sodek and Wilson, 1971) and is composed of γ-, β-, and -zeins (Esen, 1987; Coleman and Larkins, 1998).

α-Zeins with 26 (19-1W) and 16 (22-1W) gene copies in maize inbred B73 constitute 60% to 70% of total zeins. γ-Zeins consist of the 50-, 27-, and 16-1W proteins, each encoded by a single gene in B73, and amount to about 20% to 25% of total zeins. The 27- and 16-1W γ-zein genes originated from a common progenitor by allotetraploidization and share high DNA sequence similarity (Xu and Messing, 2008). The 50-1W γ-zein gene has low similarity to the other two γ-zein genes and its protein is barely detectable by SDS-PAGE (Woo et al., 2001). The 15-kD β-zein protein is encoded by a single gene and its product makes up 5% to 10% of total zeins (Thompson and Larkins, 1994). The 18- and 10-kD δ-zein proteins are also each encoded by a single gene and make up less than 5% of total zeins (Wu et al., 2009). From an evolutionary point of view, the α- and δ-zeins arose more recently, while the γ- and β-zeins are older and conserved across different subfamilies of the *Poaceae* (Xu and Messing, 2009).

Zeins are specifically synthesized in the endosperm about 10 days after pollination (DAP) on polyribosomes of the rough endoplasmic reticulum (RER), and the proteins are subsequently translocated into the lumen of the RER, where they assemble into protein bodies (Wolf et al., 1967; Larkins and Dalby, 1975; Burr and Burr, 1976; Lending and Larkins, 1992). Typical protein bodies at 18 to 20 DAP are spherical, discrete, 1 to 2 µm in diameter, and have a highly ordered architecture. α-Zeins and δ-zeins are deposited in the center of the protein body, while γ- and β-zeins are located in the peripheral layer (Ludevid et al., 1984; Lending and Larkins, 1989). Disturbance of the correct arrangement of zeins can result in irregular protein body shapes and opaque seed phenotypes (Coleman et al., 1997; Gillikin et al., 1997; Kim et al., 2004, 2006). However, the role of depletion of each class of zeins on the elaboration of protein bodies has not been studied because of the lack of natural mutants. Moreover, most existing opaque and floury mutants of maize have pleiotropic effects, which interfere with the determination of the role of storage proteins themselves.

Quality protein maize (QPM) is a high lysine-containing corn that is based on genetic modification of the opaque2 (o2) mutant. The O2 gene encodes a transcriptional activator of a subset of α-zein genes. Reduced levels of these proteins are compensated by the increased levels of lysine-rich proteins, thereby increasing the levels of lysine in the maize kernel. However, the non-vitreous phenotype of o2 makes the kernel soft, preventing commercial application because corn has to be stored in elevators and transported in large ship containers. Non-vitreous seeds are fragile and more vulnerable to fungal infection. In QPM, modifier genes convert the starchy endosperm of o2 to the vitreous phenotype of normal maize. There are multiple, unlinked o2 modifier loci (Opm) in QPM and their nature and mode of action are unknown. For conversion of elite lines into QPM, breeders first have to make both parental lines, used in hybrid seed production, homozygous for o2, and then convert them into QPM, respectively. During this process, breeders have to monitor the recessiveness of o2 and the presence of Mot, a lengthy process that discourages the spread of the benefits of QPM to consumers.

Although QPM breeding represents an advance compared to normal corn, resulting corn strains still exhibit relatively low protein content when compared to soybeans. Typical yellow dent maize contains 10% protein (Flint-Garcia et al, 2009), of which the essential amino acid lysine is only around 2% (Mertz et al, 1964), whereas soybean has 35% protein with sufficient levels of lysine. Therefore, maize meal is always supplemented with soybean in feed to meet the protein and lysine needs of livestock. However, soybean production is four times more expensive than corn. To take advantage of the cost difference, a well-known long-term selection-experiment was initiated in 1896 by C. G. Hopkins at the University of Illinois (Hopkins, 1899) and has lasted for more than a century (Dudley, 2007; Dudley & Lambert, 2004; Moose et al, 2004), yielding four strains, Illinois High Protein (IHP), Low protein (ILP), Reverse High protein (IRHP) and Reverse Low Protein (IRLP). Introgressed QTLs are capable of raising the protein concentration in IHP more than twice that in normal maize, with the most increased fraction being the alcohol-soluble proteins or prolamins. However, because the bulk of the protein consists of the lysine-poor prolamins, IHP corn could also not be commercialized. Despite all these efforts with QPM and IHP, it seems that breeders could not combine all three traits, high-lysine, hard endosperm, and high protein. Clearly a need exists in the art for improved methods to select for high-lysine, hard endosperm, and high protein and accelerate the introgression of these traits into any local germplasm.

SUMMARY OF THE INVENTION

In accordance with one embodiment of the present invention, a method for rapid and accelerated breeding of quality protein maize is provided. An exemplary method entails providing seeds from a plant comprising an RNAi construct which acts in a dominant fashion to down modulate expression of alpha zein, said down modulation decreasing the vitreous nature of seeds obtained from said plant; propagating the seed and crossing the resulting plant with a QPM plant line thereby producing kernels which exhibit increased vitreousness, increased vitreousness providing a dominant phenotype for elevated lysine and rapid selection of QPM. The method can further comprise crossing plants obtained from the resulting QPM lines with a non QPM line, thereby promoting introgression of the QPM trait into the non-QPM line. QPM trait not only restores kernel vitreousness, but also kernel hardness. In one aspect, the reduced expression of the zein protein results in an increase in the seed of an amount of at least one amino acid, which is essential to the diet of animals and humans. In order to facilitate selection of transgenic kernels, the RNAi construct is contained within an expression cassette, which also comprises at least one selectable marker and a visible reporter gene. In a preferred embodiment, the RNAi effective to down modulate alpha zein is contained in the construct shown in FIG. 6.

In yet another aspect of the invention, the method may further comprise breeding a transgenic plant from the harvested kernels to yield a progeny plant that has an increase in the amount of at least one amino acid as a dominant trait. In yet another approach, the method comprises backcrossing the progeny plant to a QPM plant line to eliminate the RNAi transgene construct. Plants obtained by such backcrosses also provide an embodiment of the invention.

In yet another aspect of the invention, another set of QTLs can be selected for that is also dominant over the RNAi, such as that shown in FIG. 6. These QTLs are independent of the QPM QTLs because they increase the nitrogen sink capacity of the seed. The elevated level of protein in the seed in the presence of the RNAi construct raises non-zein proteins to a level with sufficient essential amino acids such that no supplementation of corn meal produced therefrom with soybeans will be necessary. Furthermore, residual levels of zeins are sufficient to provide for a hard endosperm. Accordingly, the inventive method provides high-lysine, high-protein, and hard endosperm corn.

Top row shows kernels with fluorescent staining while the lower one does not, indicating the expression of the GFP reporter gene. Lower row, non-stained kernels produce the typical non-vitreous kernel of maize like in the o2 mutant. Panel C: Instead of the hybrid B73×Mo17, p6z1RNAi is crossed with a CIMMYT QPM line (Pool 42). Top row shows kernels with fluorescent staining while the lower one does not, indicating the expression of the GFP reporter gene. Lower row, non-stained kernels produce the typical vitreous kernel of maize as shown in Panel A. Despite the reduction of alpha zeins the modifiers can produce a normal kernel as in the standard American hybrids.

Figure 13:
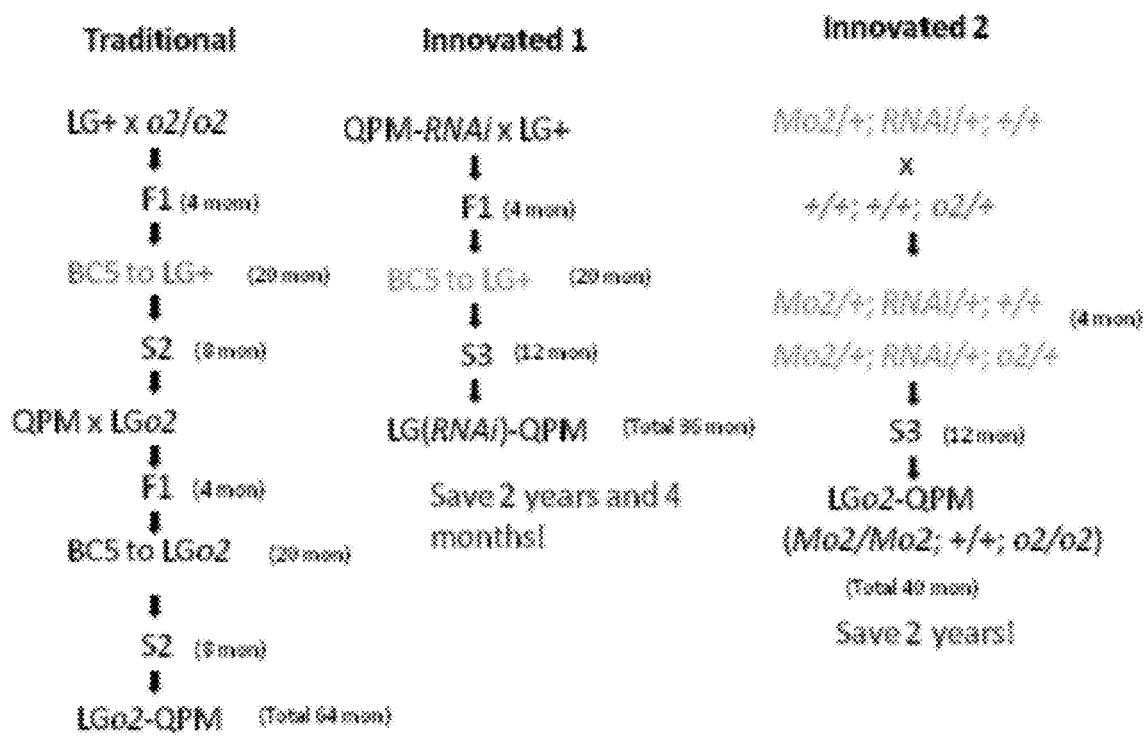

FIG. 13: Breeding scheme using the plasmid p6z1RNAi. Local germplasm refers to any maize inbred that is used for commercial production. Traditional breeding requires 64 months assuming a 4 months breeding cycle (left panel). Middle panel illustrates a breeding scheme, where the p6z1RNAi is left to reduce alpha zeins. The right panel illustrates the replacement of the transgene by a natural o2 mutation, leaving the product free of any transgenics.

Figure 14:
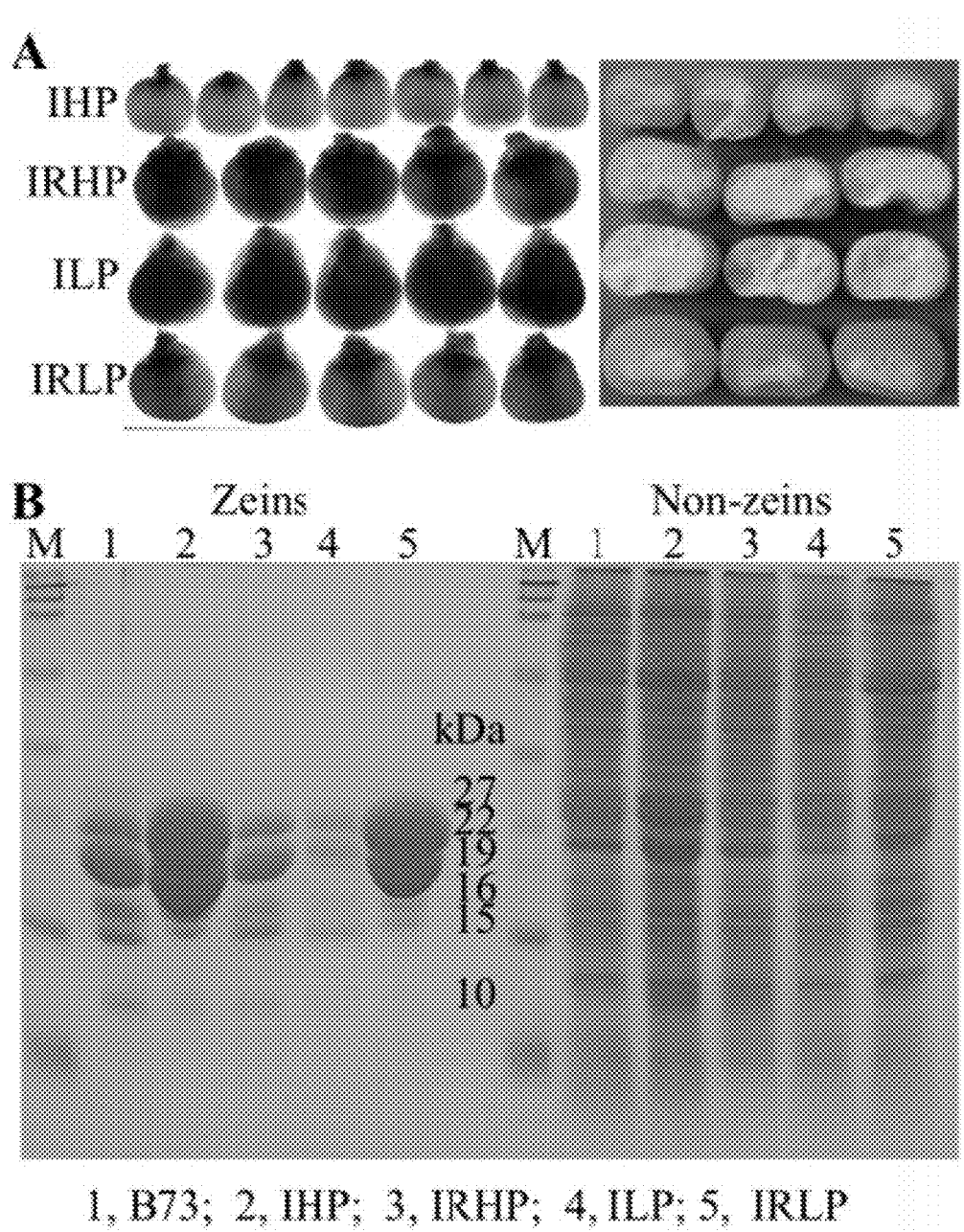

FIG. 14: Kernel phenotype and protein accumulation pattern of Illinois Protein Strains. (A) Kernel translucency and vitreousness of IHP, IRHP, ILP and IRLP. (B) Zein and non-zein accumulation pattern of B73, IHP, IRHP, ILP and IRLP analyzed by 15% SDS-PAGE. Protein from 500 µg of maize flour was loaded in each lane. M, protein markers from top to bottom being 250, 150, 100, 75, 50, 37, 25, 20, 15 and 10 kDa. The size of each zein band is indicated with numbers in the "kDa" column.

Figure 15:
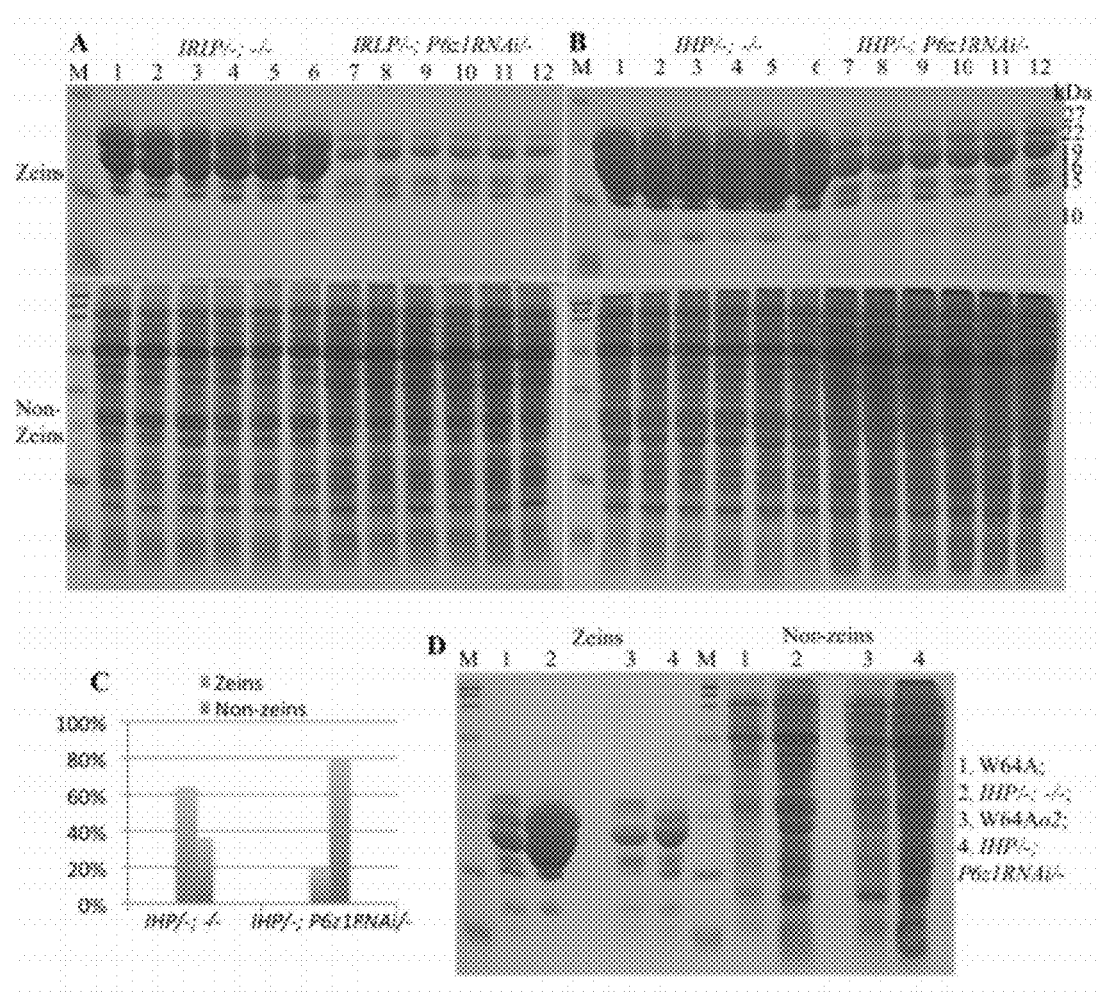

FIG. 15: Rebalancing of zein and non-zein ratio in IRLP and IHP. Zeins and non-zeins extracted from six "non-green" and "green" kernels (lanes 1-6 and 7-12, respectively), each from IRLP×P6z1RNAi/− (A) and IHP×P6z1RNAi/− (B). They were scored for GFP with fluorescent light microscope and analyzed individually by 15% SDS-PAGE. (C) Comparison of zein and non-zein ratio in total protein between IHP/−; −/− and IHP/−; P6z1RNAi/−. (D) Comparison of zein and non-zein accumulation patterns in W64A, W64Ao2, IHP/−; −/− and IHP/−; P6z1RNAi/−. The total protein loaded in each lane was equal to 500 µg of maize flour. M, protein markers in the top panels of (A) and (B) from top to bottom being 37, 25, 20, 15 and 10 kDa, and in (D) and the bottom panels of (A) and (B) being 250, 150, 100, 75, 50, 37, 25, 20, 15 and 10 kDa. The size for each zein band is marked with numbers in the "kDa" column.

Figure 16:
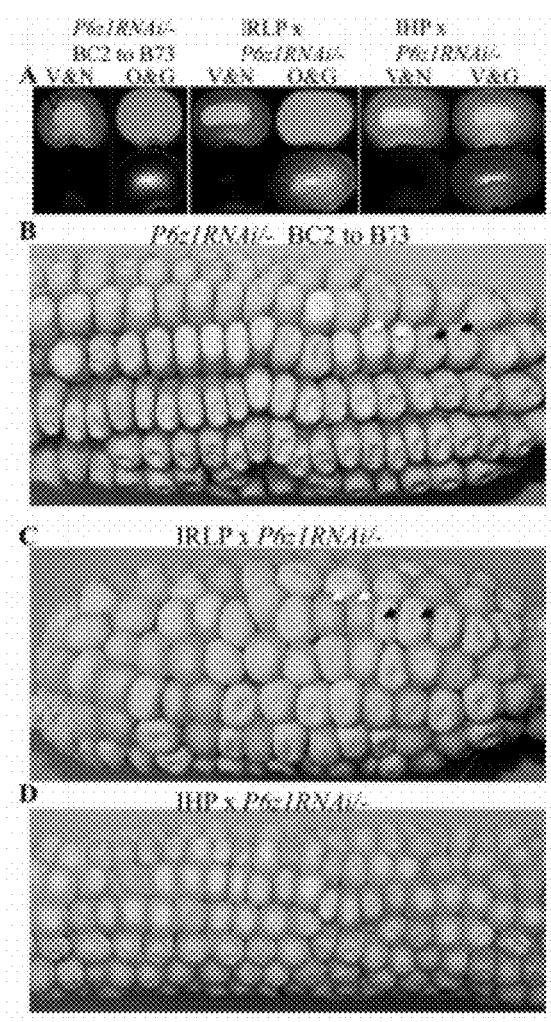

FIG. 16: Ear phenotype of P6z1RNAi backcrossed to B73, IRLP and IHP. (A) Kernels were cut in half for observation under a natural light (upper panel) and fluorescence dissection microscope (bottom panel). Opaque phenotype in kernels from the ear with P6z1RNAi backcrossed to B73 for two generations and IRLP×P6z1RNAi/− is linked to the expression of GFP. In IHP×P6z1RNAi/−, the non-green and green kernels are both vitreous. V&N, vitreous and non-green; O&G, opaque and green; V&G, vitreous and green; The ear with P6z1RNAi backcrossed to B73 for two generations (B) and IRLP×P6z1RNAi/− (C) show 1:1 ratio of vitreous and opaque segregation. Two vitreous and opaque kernels in each ear are indicated by white and black arrows, respectively. (D) In IHP×P6z1RNAi/−, kernels were uniformly vitreous.

Figure 17:
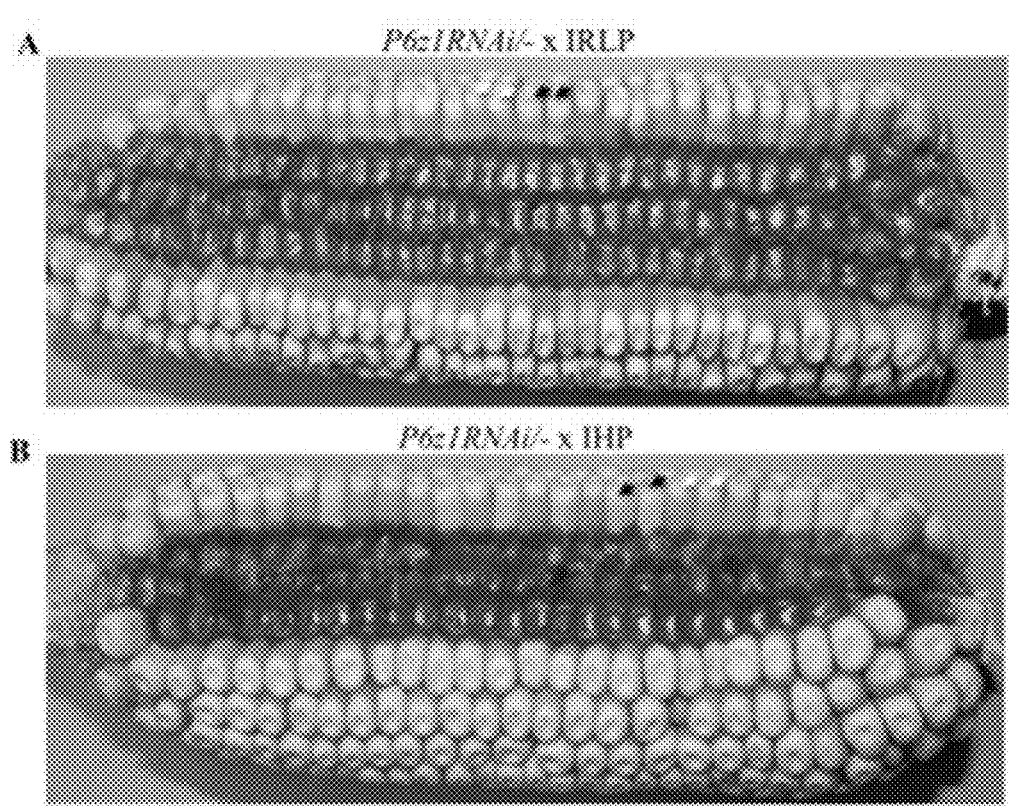

FIG. 17: Ear phenotype of P6zRNAi/−X IRLP (A) and p6z1RNAi/−X IHP (B) Vitreous and opaque kennels are indicated by white and black arrows respectively.

DETAILED DESCRIPTION OF THE INVENTION

Essential amino acids like lysine and tryptophan are deficient in corn meal because of the abundance of zein storage proteins that lack these amino acids. A natural mutant, opaque 2 (o2), causes reduction of zeins, an increase of non-zein proteins, and as a consequence, a doubling of lysine levels. However, o2's soft inferior kernels precluded its commercial use. Breeders subsequently overcame kernel softness, selecting several quantitative loci (QTLs), called o2 modifiers, without losing the high-lysine trait. These maize lines are known as "quality protein maize" (QPM). One of the QTLs is linked to the 27-kDa γ-zein locus on chromosome 7S. Moreover, QPM lines have 2- to 3-fold higher levels of the 27-kDa γ-zein, but the physiological significance of this increase was not known. Because the 27- and 16-kDa γ-zein genes are highly conserved in DNA sequence, we introduced a dominant RNAi transgene into a QPM line (CM105Mo2) to eliminate expression of them both. Elimination of γ-zeins disrupts endosperm modification by o2 modifiers, indicating their hypostatic action to γ-zeins. Abnormalities in protein body structure and their interaction with starch granules in the F1 with Mo2/+; o2/o2; γRNAi/+ genotype suggests that γ-zeins are essential for restoring protein body density and starch grain interaction in QPM. To eliminate pleiotropic effects caused by o2, the 22-kDa α-zein, γ-zein, and β-zein RNAis were stacked, resulting in protein bodies forming as honeycomb-like structures. We are unique in presenting clear demonstration that γ-zeins play a mechanistic role in QPM, providing a previously unexplored rationale for molecular breeding.

Quality Protein Maize (QPM) contains nearly twice as much usable protein as other maize (or corn) grown in the tropics and yields 10% more grain than traditional varieties of maize. The compositions and methods disclosed herein provide for the rapid production of QPM from a variety of different lines of maize. For conversion of elite lines into QPM, breeders first have to make both parental lines homozygous for o2, and then convert them into QPM, respectively. During this process, breeders have to monitor the recessiveness of o2 and the presence of Mot, a lengthy process that discourages the spread of the benefits of QPM to consumers. However, we also observed that Mots were dominant over an RNAi against alpha zeins, presumably because of over-expression of γ-zeins. Because this dominance eliminates the opaque phenotype as a marker for high-lysine, we linked the alpha zein RNAi to a GFP marker. Using this visible marker, we developed a universal and accelerated QPM conversion approach, which is described in greater detail below.

We also discovered another set of QTLs that are dominant over the alpha zein RNAi. These QTLs have been selected in a maize line, called IHP, and give rise to high levels of protein in maize comparable to those in soybeans. The high levels of protein permit us to capture more nitrogen that is produced during photosynthesis and deposited into seeds during senescence. In this sense, the leaves are the source and the seeds are the sink. The nature of these QTLs became clear, when the alpha zeinRNAi transgene was capable in reducing alpha zeins without reducing the total protein in the seed. Therefore, the QTLs were rebalancing the protein levels with non-zein proteins, which have higher levels of essential amino acids. Moreover, the same reduction in IRLP produced a soft endosperm, but retained a hard endosperm in IHP, indicating a threshold level of reduction as beneficial. Such a threshold is a typical feature of QTLs. Therefore, without knowing the molecular nature of these QTLs, the alpha zein RNAi linked to the GFP provides a unique tool for selecting maize with superior nutritional quality.

DEFINITIONS

As used herein, "genetically modified" or "genetically altered" means the modified expression of a seed protein resulting from one or more genetic modifications; the modifications including but not limited to: recombinant gene technologies, induced mutations, and breeding stably genetically modified plants to produce progeny comprising the altered gene product.

Transgenic plants producing seeds and grain with altered zein protein content are also provided.

The term "decreased" is intended to mean that the measurement of a parameter is changed by at least 10%, 20%, 30%, 40%, 50%, 60%, 70%, 80%, 90%, 100%, 200% or more when compared to the measurement of that parameter in a suitable control.

The "energy value", or "caloric value" of a feed or food, which is determined by energy density or gross energy (GE) content and by energy availability, is also termed "metabolizable energy (ME) content." (see Wiseman, J., and Cole, D. J. A., (1987), Animal Production 45(1):117-122).

As used herein, "energy availability" means the degree to which energy-rendering nutrients are available to the animal, often referred to as energy conversion (ratio of metabolizable energy content to gross energy content). One way energy availability may be determined is with in vivo balance trials, in which excreta are collected by standard methodology (e.g., Sibbald, I. R., Poultry Science, 58(5): 1325-29 (1979); McNab and Blair, British Poultry Science 29(4):697-708 (1988)). Energy availability is largely determined by food or feed digestibility in the gastro-intestinal tract, although other factors such as absorption and metabolic utilization also influence energy availability.

"Digestibility" is defined herein as the fraction of the feed or food that is not excreted in feces or urine. Digestibility is a component of energy availability. It can be further defined as digestibility of specific constituents (such as carbohydrates or protein) by determining the concentration of these constituents in the foodstuff and in the excreta. Digestibility can be estimated using in vitro assays, which is routinely done to screen large numbers of different food ingredients and plant varieties. In vitro techniques, including assays with rumen inocula and/or enzymes for ruminant livestock (e.g. Pell and Schofield, Journal of Dairy Science 76(4): 1063-1073 (1993)) and various combinations of enzymes for monogastric animals reviewed in Boisen and Eggum, Nutrition Research Reviews 4:141-162 (1991) are also useful techniques for screening transgenic materials for which only limited sample is available.

The compositions and methods of the invention are useful for modulating the levels of at least one seed protein in seeds. "Modulate" is defined herein as an increase or decrease in the level of a seed protein within seed of a genetically altered plant relative to the level of that protein in seed from the corresponding wild-type plant (i.e., a plant not genetically altered in accordance with the methods of the present invention).

The terms "inhibit," "inhibition," "inhibiting", "reduced", "reduction" and the like as used herein refer to any decrease in the expression or function of a target gene product, including any relative decrement in expression or function up to and including complete abrogation of expression or function of the target gene product.

The term "expression" as used herein in the context of a gene product refers to the biosynthesis of that gene product, including the transcription and/or translation of the gene product. Inhibition of expression or function of a target gene product (i.e., a gene product of interest) can be in the context of a comparison between any two plants, for example, expression or function of a target gene product in a genetically altered plant versus the expression or function of that target gene product in a corresponding wild-type plant. Alternatively, inhibition of expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product.

The term "inhibitory sequence" encompasses any polynucleotide or polypeptide sequence that is capable of inhibiting the expression of a target gene product, for example, at the level of transcription or translation, or which is capable of inhibiting the function of a target gene product. Exemplary constructs encoding such inhibitory sequences are disclosed herein.

When the phrase "capable of inhibiting" is used in the context of a polynucleotide inhibitory sequence, it is intended to mean that the inhibitory sequence itself exerts the inhibitory effect; or, where the inhibitory sequence encodes an inhibitory nucleotide molecule (for example, hairpin RNA, miRNA, or double-stranded RNA polynucleotides), or encodes an inhibitory polypeptide (i.e., a polypeptide that inhibits expression or function of the target gene product), following its transcription (for example, in the case of an inhibitory sequence encoding a hairpin RNA, miRNA, or double-stranded RNA polynucleotide) or its transcription and translation (in the case of an inhibitory sequence encoding an inhibitory polypeptide), the transcribed or translated product, respectively, exerts the inhibitory effect on the target gene product (i.e., inhibits expression or function of the target gene product).

Conversely, the terms "increase", "increased," and "increasing" in the context of the methods of the present invention refer to any increase in the expression or function of a gene product, including any relative increment in expression or function.

In many instances the nucleotide sequences for use in the methods of the present invention, are provided in transcriptional units with for transcription in the plant of interest. A transcriptional unit is comprised generally of a promoter and a nucleotide sequence operably linked in the 3' direction of the promoter, optionally with a terminator.

"Operably linked" refers to the functional linkage between a promoter and a second sequence, wherein the promoter sequence initiates and mediates transcription of the DNA sequence corresponding to the second sequence. The expression cassette will include 5' and 3' regulatory sequences operably linked to at least one of the sequences of the invention.

Generally, in the context of an over expression cassette, operably linked means that the nucleotide sequences being linked are contiguous and, where necessary to join two or more protein coding regions, contiguous and in the same reading frame. In the case where an expression cassette contains two or more protein coding regions joined in a contiguous manner in the same reading frame, the encoded polypeptide is herein defined as a "heterologous polypeptide" or a "chimeric polypeptide" or a "fusion polypeptide". The cassette may additionally contain at least one additional coding sequence to be co-transformed into the organism. Alternatively, the additional coding sequence(s) can be provided on multiple expression cassettes.

The methods of transgenic expression can be used to decrease the level of at least one seed protein in grain. The methods of transgenic expression comprise transforming a plant cell with at least one expression cassette comprising a promoter that drives expression in the plant operably linked to at least one nucleotide sequence encoding an RNAi that inhibits production of the desired seed protein. Methods for expressing transgenic genes in plants are well known in the art.

Plant transformants containing a desired genetic modification as a result of any of the above described methods resulting in decreased or eliminated expression of the seed protein of the invention can be selected by various methods known in the art. These methods include, but are not limited to, methods such as SDS-PAGE analysis, immunoblotting using antibodies which bind to the seed protein of interest, single nucleotide polymorphism (SNP) analysis, or assaying for the products of a reporter or marker gene, and the like.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. GFP is exemplified herein. The nucleic acid may be either RNA or DNA, linear or circular, single or double stranded, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The following materials and methods are provided to facilitate the practice of the present invention. They are not intended to limit the invention in any way.

Genetic Stocks.

Maize inbred line CM105+, its o2 mutant CM105o2, and the modified o2 mutant CM105Mo2 have been reported previously (24). We also used Pool42 from CIMMYT as a source for QPM. CM 105 wild-type, o2 and Mot were grown in the field in Lincoln, Nebr. in summer, 2009. The z1CRNAi (for knockdown of the 22-kDa α-zeins), γRNAi (for knockdown of the 27- and 16-kDa γ-zeins), and βRNAi (for knockdown of the 15-kDa β-zein) were generated previously (9, 16). Briefly, The RNAi transcripts were driven by the 27-1W gamma-zein promoter amplified from maize inbred line B73 with the primer pair P27-EcoR1 and p27-Xma1; the inverted 15-kD β-zein and 27-kD gamma-zein coding sequences were amplified by two pairs of primers, 15kD-Xma1/15kD-BspE1 and 15kD-BglII/15kD-Xba1 as well as 27kD-Xma1/27kD-BspE1 and 27 kD-BglII/27kD-Xba1, respectively. The inverted 27-kD gamma-zein and 15-kD β-zein genes were separated by the GFP-coding sequence in order to form a loop in the RNAi transcripts. It was amplified from the plasmid pEGFP (Clontech) with the primer pair GFP-BspE1 and GFP-BglII. T35S was amplified from the plasmid PTF102 with the primer pair T35S-Xba1 and T35S-HindIII. The ligations of these fragments were conducted in T-Easy vector (Promega) and then transferred into the binary vector PTF102.

The RNAi constructs were delivered into maize by Agrobacterium tumefaciens-mediated transformation. Hi-II F1 (B×A) immature embryos (1.5-2.0 mm) were dissected from the ears growing in the chamber (Waksman Institute) at 10 to 11 DAP. All subsequent steps were performed according to the protocol of Frame et al. (2002). When the transgenic seedlings were transferred to the soil, a small piece of leaf was cut to extract genomic DNA by the cetyl-trimethyl-ammonium bromide method. The positive transformation events could be confirmed by PCR with the primer pair GFPF and T35S-HindIII. The RNAi construct segregation in the next generation was also analyzed with this primer pair.

The z1C (the 22-kD α-zein genes) RNAi event has been reported previously (Segal et al., 2003).

TABLE 1

List of primers.

| Primer name | Sequence |
| --- | --- |
| P27-EcoR1 | 5'-CCAGAATTCCTTTATAATCAACCCGCACTC-3' |
| p27-Xma1 | 5'-AATCCCGGGACCATGGTGTCGATCGGGTTC-3' |
| 15kD-Xma1 | 5'-ATTCCCGGGTCAGTAGTAGGGCGGAATG-3' |
| 15kD-BspE1 | 5'-ATATCCGGATGAAGATGGTCATCGTTC-3' |
| 15kD-BglII | 5'-ATTAGATCTATGAAGATGGTCATCGTTC-3' |
| 15kD-Xba1 | 5'-AATTCTAGATCAGTAGTAGGGCGGAATG-3' |
| 27kD-Xma1 | 5'-ATTCCCGGGACTCAACTAGCTAGCTAGCC-3' |
| 27kD-BspE1 | 5'-ATATCCGGATGAGGGTGTTGCTCGTTGC-3' |
| 27kD-BglII | 5'-ATTAGATCTATGAGGGTGTTGCTCGTTGC-3' |
| 27kD-Xba1 | 5'-AATTCTAGAACTCAACTAGCTAGCTAGCC-3' |
| GFP-BspE1 | 5'-ATATCCGGATGGATCCATGGTGAGCAAGGGCGAG-3' |
| GFP-BglII | 5'-ATTAGATCTTGAGCTCTTACTTGTACAGCTCGTCC-3' |
| T35S-Xba1 | 5'-ATATCTAGAACTGCAGCGGCGCAAAAATCACCAGTC-3' |
| T35S-HindIII | 5'-ATTAAGCTTTGCAGGTCACTGGATTTTGG-3' |
| GFPF | 5'-ACAACCACTACCTGAGCAC-3' |
| qactinF | 5'-GTTCGACATGGTACGTCAG-3' |
| qactinR | 5'-ATTGGAGCCAGTGCTACTG-3' |
| q15F | 5'-TGGGTGGACTCTACCAGTAC-3' |
| q15R | 5'-ATGGATAGAGGAGATTTCCC-3' |
| q27F | 5'-AGCCTCATCCCCAGCCAC-3' |
| q27R | 5'-AGGTTCCCTGCAGCTGGC-3' |
| q16F | 5'-ATACCCCACTCAACCACCG-3' |
| q16R | 5'-GCAGGATCCGAACTGCTG-3' |
| q50F | 5'-GCAATCTTGACAGCAGCAC-3' |
| q50R | 5'-TGTCATTGCTGCTGCATGG-3' |
| dzs18-10F | 5'-TTTGCGCTCCTAGCTCTTTG-3' |
| dzs18-10R | 5'-TATCTAGAATGCAGCACCAAC-3' |

Total Zein Extraction.

Immature kernels at 18 DAP were harvested. The embryos were saved for extraction of DNA individually. The genotype of each kernel with respect to the γRNAi gene was confirmed by PCR with primer pair 5'-ACAACCACTAC- CTGAGCAC-3' and 5'-ATTAAGCTTTGCAGGTCACTG-GATTTTGG-3', which has been described elsewhere (9). Each endosperm was cut into two halves. One was fixed for transmission or scanning electron microscopy. The other half (≈50 mg) was used for zein extraction. The finely ground endosperm was mixed and vortexed with 400 µL, of 70% ethanol/2% 2-mercaptoethanol (vol/vol), then kept on the bench at room temperature for 2 h; the mixture was centrifuged at 13,000 rpm (Eppendorf, Centrifuge 5417C) in a microfuge for 10 min, then 200 µL, of the supernatant liquid was transferred to a new tube; 10 µL of 10% SDS was added to the extract, the mixture was dried by vacuum, and resuspended in 100 µL of distilled water. Next, 2 µL (equal to 500-µg endosperm powder) of each sample was analyzed by 15% SDS/PAGE gel.

Stacking of ZeinRNAiTransgenes.

The QPM CM105Mo2 was pollinated by the F1 progeny of W64Ao2×γRNAi or W64Ao2×(γRNAi×βRNAi). The triple stack of the z1CRNAi, γRNAi, and βRNAi was generated from reciprocal crosses between a homozygous z1CRNAi plant and a double stack of γRNAi and γRNAi.

Transmission and Scanning Electron Microscopy.

Previously published methods were used with some modifications (34, 44). Two 2-mm thick sections were sliced perpendicular to the aleurone layer to include the pericarp, aleurone, and 10 to 20 cell layers of the endosperm. All these slices were fixed in 5% glutaraldehyde in 0.1 M sodium cacodylate buffer, pH 7.4, containing 2% sucrose, in a 2-mL tube. Fixation was kept at 4° C. overnight and for another 3 h at room temperature. The tissues were rinsed for 2 to 3 h with several changes of 0.1 M sodium cacodylate buffer containing decreasing amounts of sucrose. They were then post-fixed in buffered 1% osmium tetroxide at 4° C. overnight followed by dehydration in a graded series of acetone washings and embedded in epon resin.

For electron microscopy, 90-nm thin sections were cut on a Leica EM UC tramicrotome. Sectioned grids were stained with saturated solution of uranyl acetate and lead citrate. Sections were analyzed at 80 Kv with a Philips CM 12 transmission electron microscope.

For scanning electron microscopy, the dehydrated 18-DAP samples were dried to a critical point, using $CO_2$ in a dryer (Balzers CPD 020); the dried samples were mounted on the surface of a brass disk using double-sided adhesive silver-tape, coated with gold/palladium by a sputter coating unit (Balzers CSD 004) and viewed on a scanning electron microscope (Amray 1830 I).

The following examples are provided to illustrate certain embodiments of the invention. They are not intended to limit the invention in any way.

Example I

Gamma-Zeins are Essential for Endosperm Modification in Quality Protein Maize

Grain hardness is a key agronomic trait in maize (Zea mays L.) because it provides resistance to damage during harvesting, transport, storage, and marketing, as well as to insect and fungal damage. Kernel texture is determined by the relative amounts of hard (vitreous) and soft (opaque, non-vitreous) endosperm and there is a positive correlation between zein storage proteins and kernel vitreousness (1). Zeins are a heterogeneous mixture of alcohol-soluble proteins, falling into four classes based on their structure (α-, β-, γ-, and δ-zeins) (2). The zeins extracted with the Osborne method (3) are classified as z1 (19- and 22-kDa α-zeins) and the cross-linked z2 group (50-, 27-, and 16-kDa γ-zeins, 15-kDa β-zein, and 18- and 10-kDa δ-zeins) (4, 5). Zeins are deposited in rough endoplasmic reticulum-delimited protein bodies (PBs) in endosperm cells from around 10 days after pollination (DAP) (6, 7). Alpha- and δ-zeins are mainly stored in the center of PBs, and γ- and β-zeins are deposited in the peripheral region (8). The Cys-rich γ- and β-zeins have redundant function in the stabilization of PB morphology (9). The translucency (vitreousness) of the mature kernel is influenced by PB composition and the spatial organization of α-, β-, γ-, and δ-zeins (10-16).

Because zeins are essentially devoid of lysine and tryptophan, their high-level accumulation results in poor grain-protein quality (17, 18). The opaque2 (o2) mutant, identified by Singleton and Jones in the 1920s (19), initially showed great promise in monogastic animal feeding trials because it was shown to have twice the normal levels of lysine and tryptophan (15). The improved nutritional value resulted from much reduced α-zein accumulation, which paradoxically caused a soft endosperm texture that ultimately prevented the commercial success of o2. Quality protein maize (QPM) was developed by selecting modified o2 lines with restored vitreous endosperm that maintained the low-α-zein, high-lysine phenotype (20).

Genetic analysis of o2 modifiers identified several disperse quantitative trait loci (QTLs). Although their molecular identities have remained unknown, QTLs could be correlated with observed increases in 27-kDa γ-zein transcript and protein in QPM (21). Unlike the 22-kDa α-zein genes, the 27-kDa γ-zein gene is not under the transcriptional control of the O2 protein (22, 23). Two different QTLs, which are candidates for o2 modifier genes, affect 27-kDa γ-zein gene expression. The first of these is associated with increased expression (24) and the other is linked to o15, a mutation at a different chromosome 7 location (25), which causes decreased 27-kDa γ-zein expression. The first QTL could be a cis-acting mutation of the 27-kDa zein gene, and the latter a trans-acting factor. In the B73 genome, single-copy γ-zein genes encode the 50-, 27-, and 16-kDa proteins (6). The 27- and 16-kDa γ-zein genes originated from a common progenitor by allotetraploidization and share high DNA and protein-sequence similarity (5). Their proteins amount to about 20 to 25% of total zeins (26); the low abundance 50-kDa γ-zein gene has low similarity to the other two γ-zein genes (6). Although the 16-kDa γ-zein expression is not elevated like the 27-kDa γ-zein gene in QPM, probably because of diverged regulation, their protein products and β-zein have redundant and unique function in protein body stabilization (9). Furthermore, neither the 27-kDa γ-zein-null mutant nor the ⊕-zein RNAi seeds showed any opaque phenotype (9, 27). When the 27- and 16-kDa γ-zeins were knocked-down by γRNAi, only partial opacity occurred (9). The opacity was strongly intensified when the γRNAi and βRNAi were combined. The opacity was not caused by reducing the thickness of the vitreous endosperm as in o2, but by an incomplete embedding of starch granules in the vitreous area (9). Because the expression of the β-zein gene is also regulated by O2 (28) and significantly reduced in QPM (29), the amount of γ-zeins would become critical to keep starch granules embedded in the vitreous area. To examine the role of γ-zeins in QPM, we used an RNAi construct designed from the inverted coding sequences of the 27-kDa γ-zein gene to knock down both 27- and 16-kDa γ-zeins by taking advantage of their DNA sequence conservation (9). Indeed, in the progeny with the genotype Mo2/+; o2/o2; γRNAi/+ from the cross of QPM with O2/o2; γRNAi/+, the modified phenotype was lost, indicating that the action of the o2 modifiers is preconditioned by the expression of γ-zeins, which is genetically described as hypostasis. In the resulting endosperm cells, although discrete PBs were still observed, larger, honeycomb-like masses of unseparated PBs were also observed. This indicated that both z1 and z2 proteins are necessary to maintain the density, integrity, and spatial separation of PBs. By stacking of the 22-kDa α-zein, γ-zein, and β-zein RNAis (designated as z1CRNAi, γRNAi, and βRNAi, respectively), which eliminated the possible pleiotropic effects caused by o2, the unseparated PB phenotype became more severe. This finding reinforces the fact that different zeins have evolved to play distinct roles in the development of the endosperm.
Segregation Analysis of Zein Accumulation Patterns of QPM by the γRNAi Line.

Figure 1:
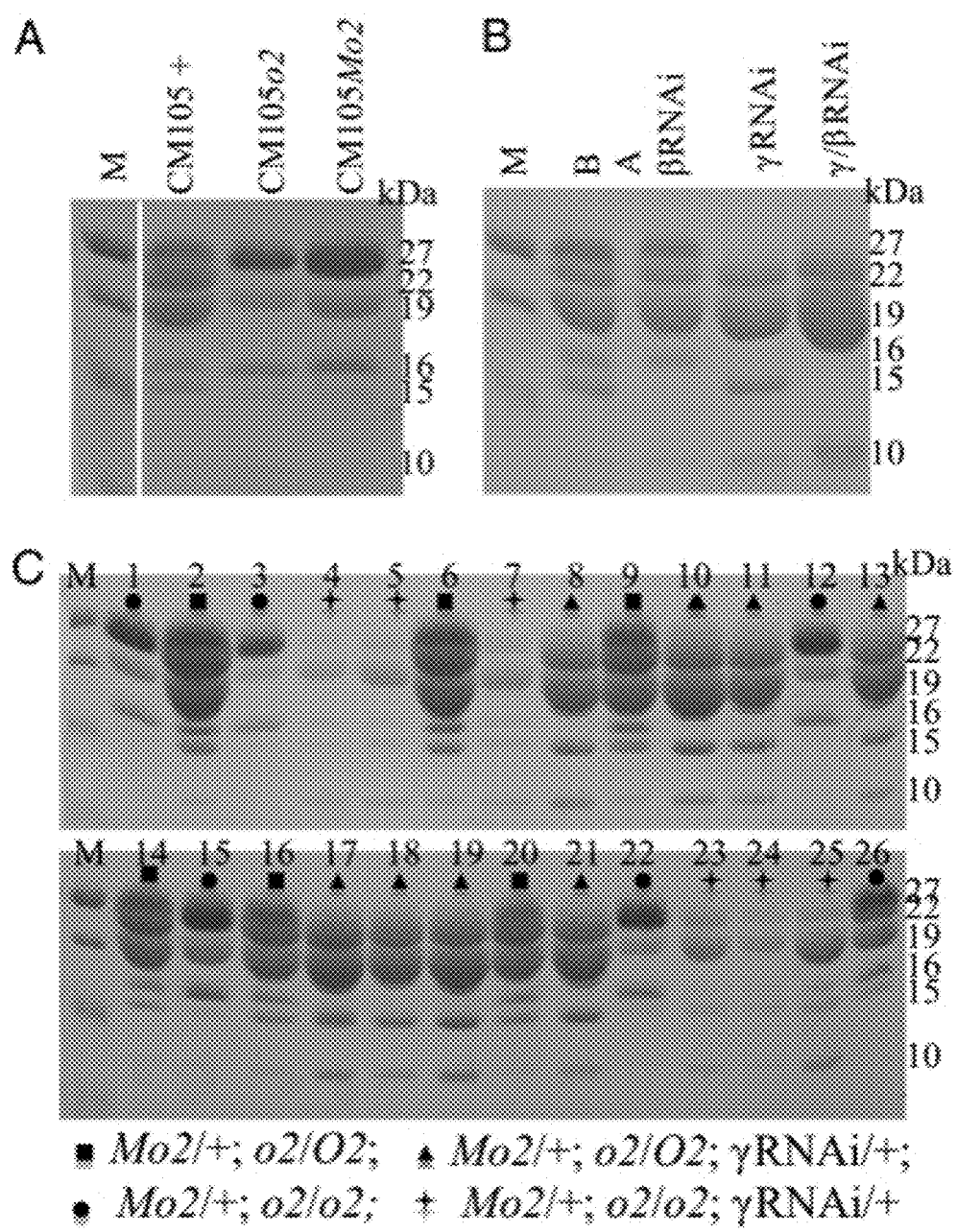
FIG. 1: Zein accumulation in normal, o2, QPM, RNAi, and their stacked mutant seeds at 18 DAP detected by SDS/PAGE. (A) CM105+, CM105o2, and CM105Mo2. The slice of protein markers run in a different gel was composited with the samples, as indicated by a white line. (B) BA (non-transgenic hybrid seed of B and A lines as a control), βRNAi, γRNAi, and the stack of the two RNAis. (C) Zein accumulation patterns for 26 kernels dissected from the cross of CM105Mo2×O2/o2; γRNAi/+. M, protein markers from top to bottom being 25, 20, 15, and 10 kDa. Total zein loaded in each lane was equal to 500 μg of fresh endosperm at 18 DAP. The size for each band is indicated by the numbers in the "kDa" columns.

The knock-down lines or natural null mutants of α-, β-, γ-, and δ-zein genes and their resulting phenotypes have been characterized previously (9, 16, 30). To test the theory that the increased γ-zein in QPM is necessary for endosperm modification, the γRNAi knock-down line described above was introduced into a QPM line. As a validation of the starting material, we compared protein levels of both parental lines by SDS/PAGE. As shown previously, total zeins extracted from CM105+, CM105o2, and CM105Mo2 at 18 DAP revealed an enhanced level of the 27-kDa γ-zein in CM105Mo2 (FIG. 1A) (31). Besides the 22-kDa α-zeins, the β-kDa also regulated by O2 (28), was markedly reduced in CM105o2 and CM105Mo2. Interestingly, the accumulation of the 19-kDa α-zeins was also significantly—although not as drastically—reduced, consistent with previous observations (29, 31, 32). As expected in the stack of the γRNAi and βRNAi, both γ- and β-zeins were knocked down to an undetectable level, and thus exhibited a highly specific inhibitory effect on zein gene expression (FIG. 1B).

Because genotypes for o2, o2 modifiers, and RNAi were recessive, semidominant, and dominant, respectively, the γRNAi was crossed with W64Ao2, and the F1 progeny were used to pollinate a QPM line, CM105Mo2. At 18 DAP, 26 kernels were dissected for extraction of total zeins. The embryo of each individual was saved to extract genomic DNA for genotyping. PCR results showed that kernels 4, 5, 7, 8, 10, 11, 13, 17, 18, 19, 21, 23, 24, and 25 inherited the γRNAi gene (14 of 26 kernels). As expected, the phenotypes of the zein accumulation patterns exhibited Mendelian segregation. Kernels 2, 6, 9, 14, 16, and 20 represented the genotype Mo2/+; o2/O2, with enhanced accumulation of the 27-kDa γ-zein and normal levels of the other zeins. Kernels 1, 3, 12, 15, 22, and 26 were genotype Mo2/+; o2/o2, with the 27-kDa γ-zein increased, and α-zeins (22- and 19-kDa) and β-zein decreased. Kernels 8, 10, 11, 13, 17, 18, 19, and 21 were selected to represent the genotype Mo2/+; o2/o2; γRNAi/+, and showed similar phenotype to Mo2/+; o2/o2, except the knock-down of the 27- and 16-kDa γ-zeins. Kernels 4, 5, 7, 23, 24, and 25 were of Mo2/+; o2/o2; γRNAi/+ genotype, and showed decreased protein accumulation not only for α- and β-zeins, but also for the 27- and 16-kDa γ-zeins. All kernels with this genotype show that the γ-RNAi transgene eliminates γ-zein expression in the presence of Mo2, suggesting a hypostatic relationship between the two.
Transmission Electron Microscopy of Endosperm from γRNAi in QPM.

Figure 2:
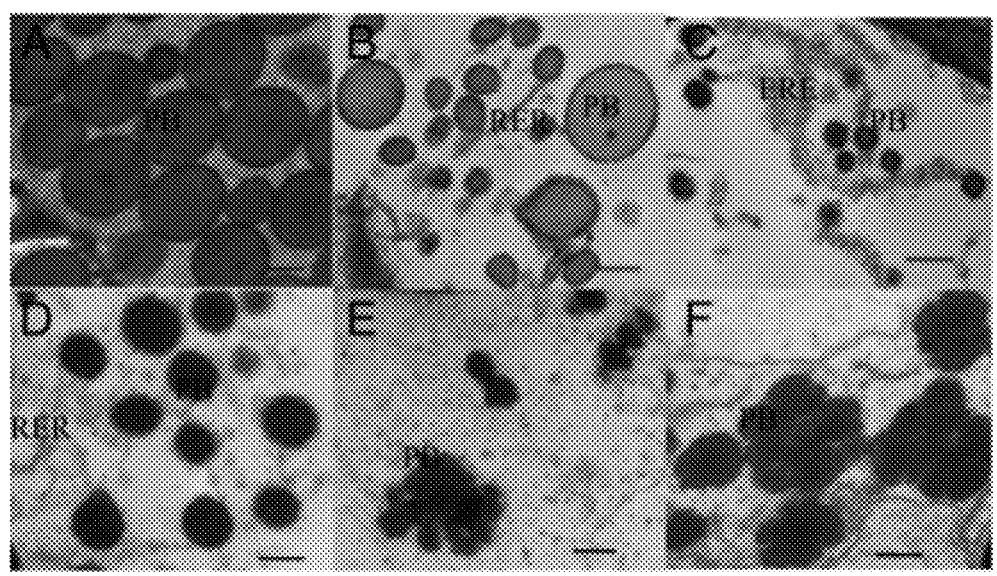
FIG. 2: Transmission electron micrographs of protein bodies in different genotypes. (A) CM105+. (B) γRNAi. (C) CM105o2. (D) CM105Mo2. (E) Mo2/+; o2/o2; γRNAi/+. (F) Mo2/+; o2/o2; γRNAi/+; βRNAi/+. (Scale bars, 500 nm.) PB, protein body; RER, rough endoplasmic reticulum.
Figure 3:
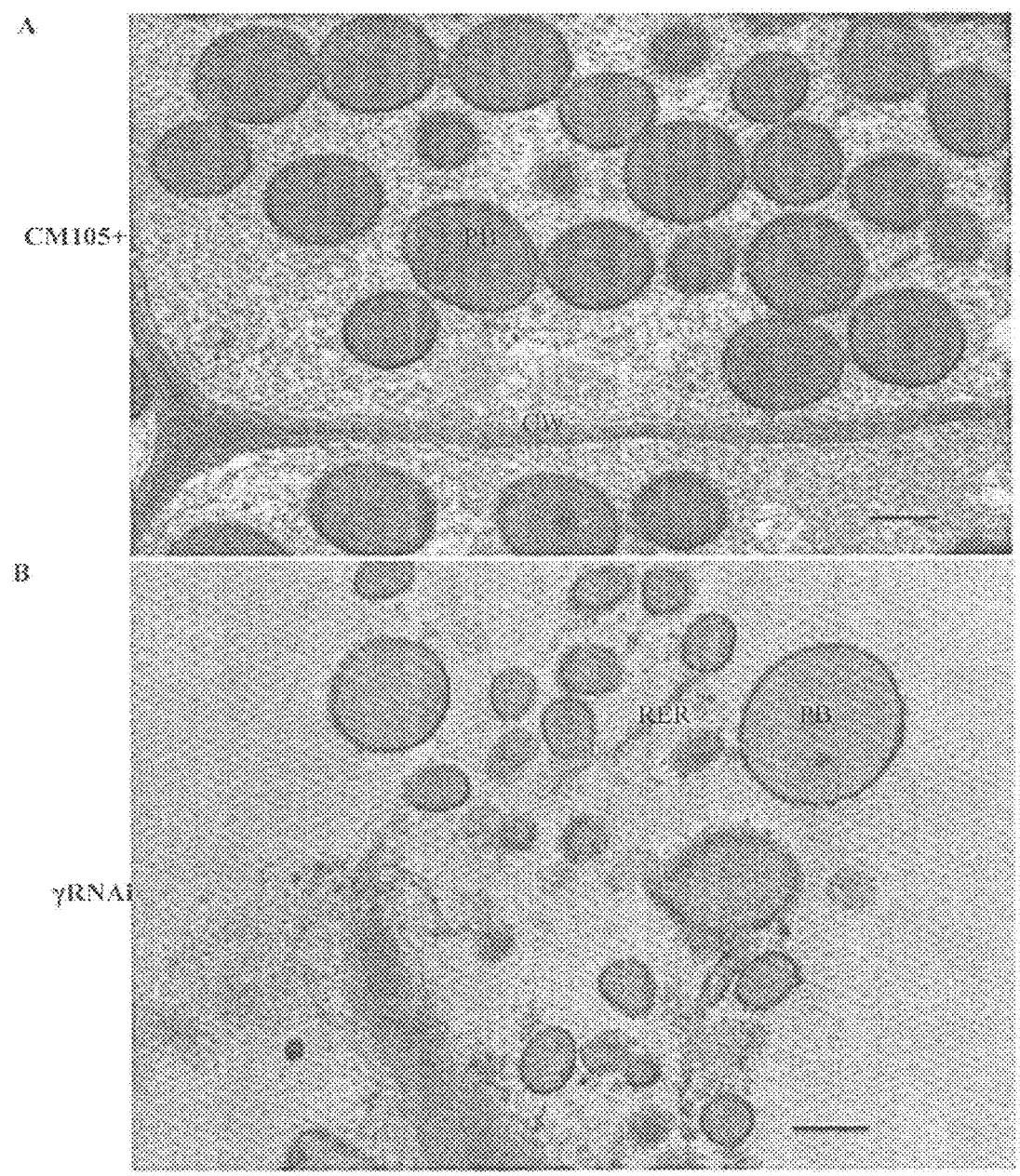
FIG. 3: Transmission electron micrographs of protein bodies in different genotypes with wider field view at 18 d after pollination. (A) CM105+. (B) γRNAi. (C) CM105o2. (D) CM105Mo2. (E) Mo2/+; o2/o2; γRNAi/+. (F) Mo2/+; o2/o2; γRNAi/+; βRNAi/+. (Scale bars, 500 nm.) CW, cell wall; Mt, mitochondria; PB, protein body; RER, rough endoplasmic reticulum.
Figure 3:
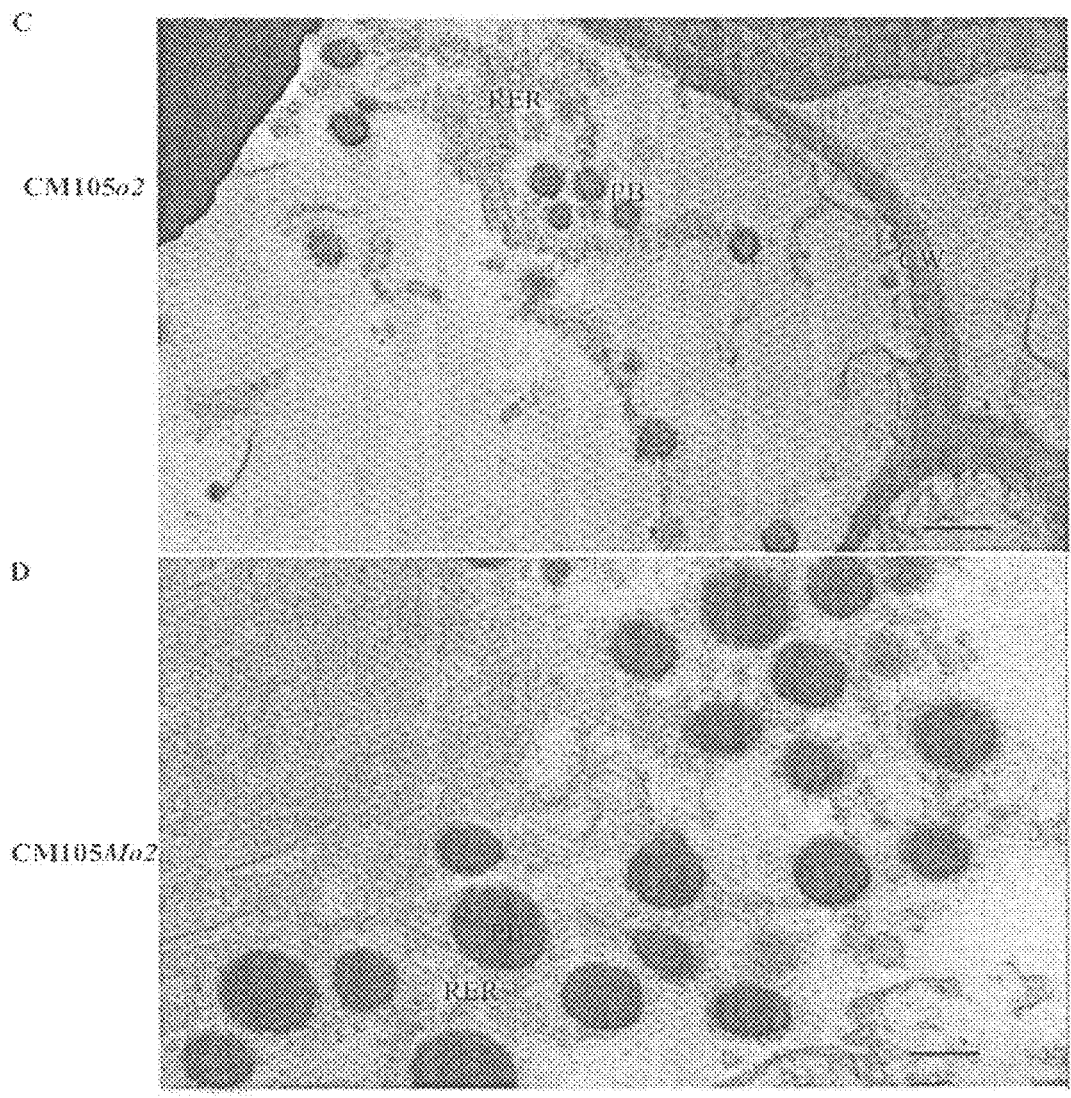
Figure 3:
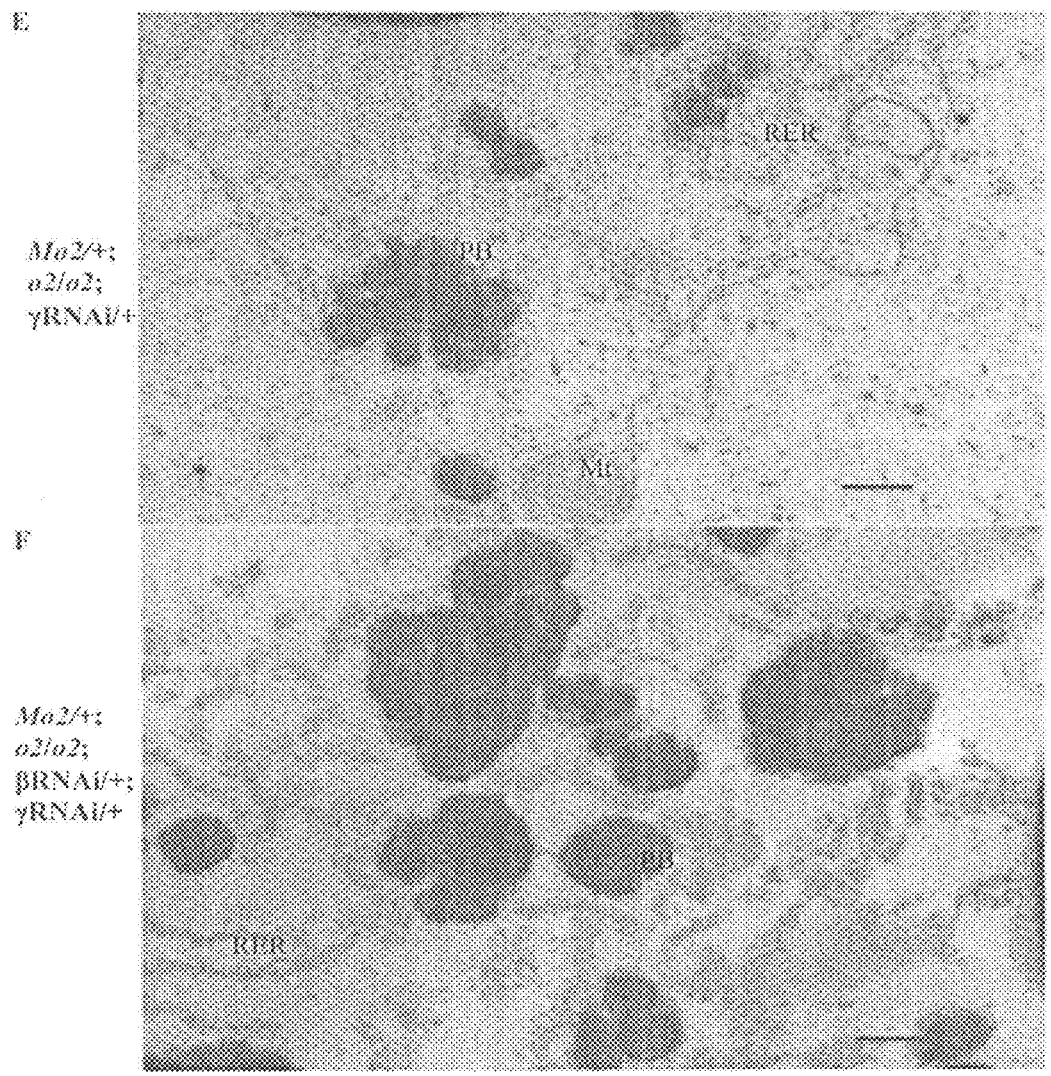

There are very specific differences in PBs between o2 and QPM. Consequently, suppression of the modifiers can also be monitored by observing the structure of PBs. Therefore, several 18-DAP kernels with the Mo2/+; o2/o2; γRNAi/+ genotype were analyzed with transmission electron microscopy. Kernels from CM105+, CM105o2, CM105Mo2, and γRNAi were used as references. As shown in FIG. 2, the normal background CM105+ exhibited round and discrete PBs, although CM105o2 developed PBs with dramatically reduced density and size (FIGS. 2 A and C and FIGS. 3 A and C) (33). In the QPM line, CM105Mo2, the average number and size of PBs were significantly larger than those in CM105o2 (FIGS. 2 C and D and FIGS. 3C and D), consistent with a previous report (21). This result could be further confirmed under scanning electron microscopy observation (FIGS. 4B and C) (31). When y-zeins were knocked down, the PBs were slightly irregular in size and morphology (FIG. 2B) (9).

A unique effect on PBs was observed when the γRNAi and the QPM properties were combined in the Mo2/+; o2/o2; γRNAi/+ genotype. PBs were no longer discrete, but appeared as multilobe irregular structures (FIG. 2E and FIG. 3E). This result has previously been observed in mutants where zeins were not properly processed, like floury2 (13, 34, 35). Interestingly, when a triple combination of γRNAi, βRNAi, and QPM was examined, these abnormal PB masses were larger and more frequently observed (FIG. 2F and FIG. 3F).
Scanning Electron Microscopy of Endosperm from γRNAi in QPM.

Figure 4:
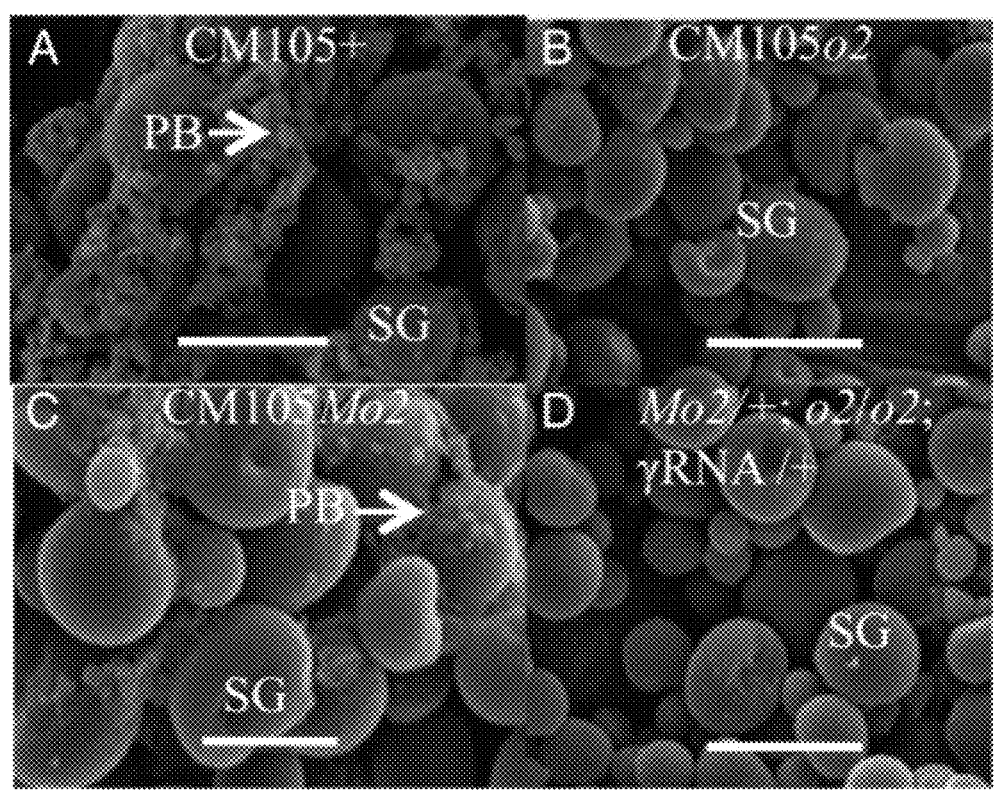
FIG. 4: Scanning electron micrographs of protein bodies in different genotypes. (A) CM105+. (B) CM105o2. (C) CM105Mo2. (D) Mo2/+; o2/o2; γRNAi/+. (Scale Bars, 10 μm.) PB, protein body; SG, starch granules.

Further examination of PBs with scanning electron microscopy permits the analysis of the interaction between PBs and starch granules, which is thought to be important in determining kernel vitreousness (36). During endosperm development, starch granules and PBs are embedded in a proteinaceouscytoskeletal matrix (31, 37). In o2 endosperm, the proteinaceous matrix is almost totally absent, resulting in loose and non-compacted starch granules (FIG. 4B), whereas in QPM, a matrix is partially restored (FIG. 4C) (31). However, the partial matrix was abolished by knockdown of y-zeins (FIG. 4D). This finding is consistent with its considerable reduction not only in α-zeins, but also γ- and β-zeins (FIG. 1C). In QPM, although PB size, number, and proteinaceous matrix were all reduced compared with wild-type endosperm, these parameters were all considerably larger than in o2 (FIG. 4C) (31). However, when the γRNAi was introduced into QPM, the resulting genotype Mo2/+; o2/o2; γRNAi/+ generated the same phenotype as the o2 mutant (FIGS. 4 B and D), where the proteinaceous matrix is completely disrupted, indicating that endosperm modification is abolished.

The elevated accumulation of the 27-kDa γ-zein in QPM endosperm is associated with an increase in the number and size of PBs, and vitreous endosperm formation in the o2 mutant background. Whether the restoration of the proteinaceous network is related to the elevated expression of 27-kDa γ-zein remains to be seen. Interestingly, uncharacterized opaque mutants, such as opaque9, exhibit no reduction in zein accumulation (38), suggesting that they might only have changes in spatial deposition of zeins in PBs, like floury1 (10), or encode cytoplasm-resident proteins that are necessary for vitreous endosperm formation during kernel maturation.

It is possible that such hypothetical proteins are increased in QPM. The modification effects of the dominantly acting o2 modifier genes on the soft o2 phenotype are completely suppressed by the γRNAi. This shows that γ-zeins are necessary for modification but does not prove that they are alone sufficient. If other genes act in concert with the γ-zeins and increase to allow modification, we propose that actions of these genes are hypostatic to the high expression of γ-zein genes.

Loss of QPM Kernel Phenotype by Knock-Down of γ-Zeins.

Figure 5:
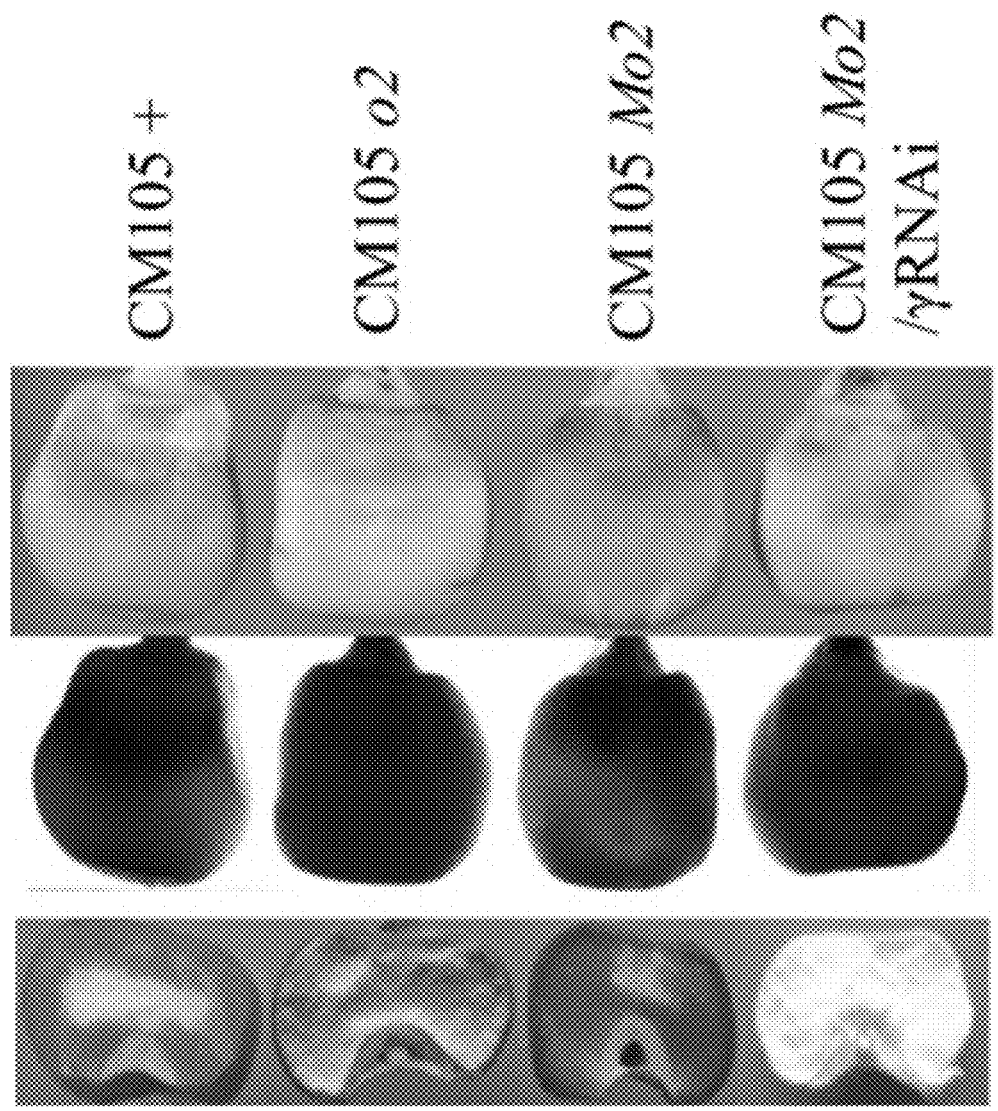
FIG. 5: Kernel phenotype for CM105+, CM105o2, CM105Mo2, and new mutant Mo2/+; o2/o2; γRNAi/+. Photographs for intact or decapped kernels were taken under incandescent light (Top and Bottom) or with transmitted light (Middle).
Figure 6:
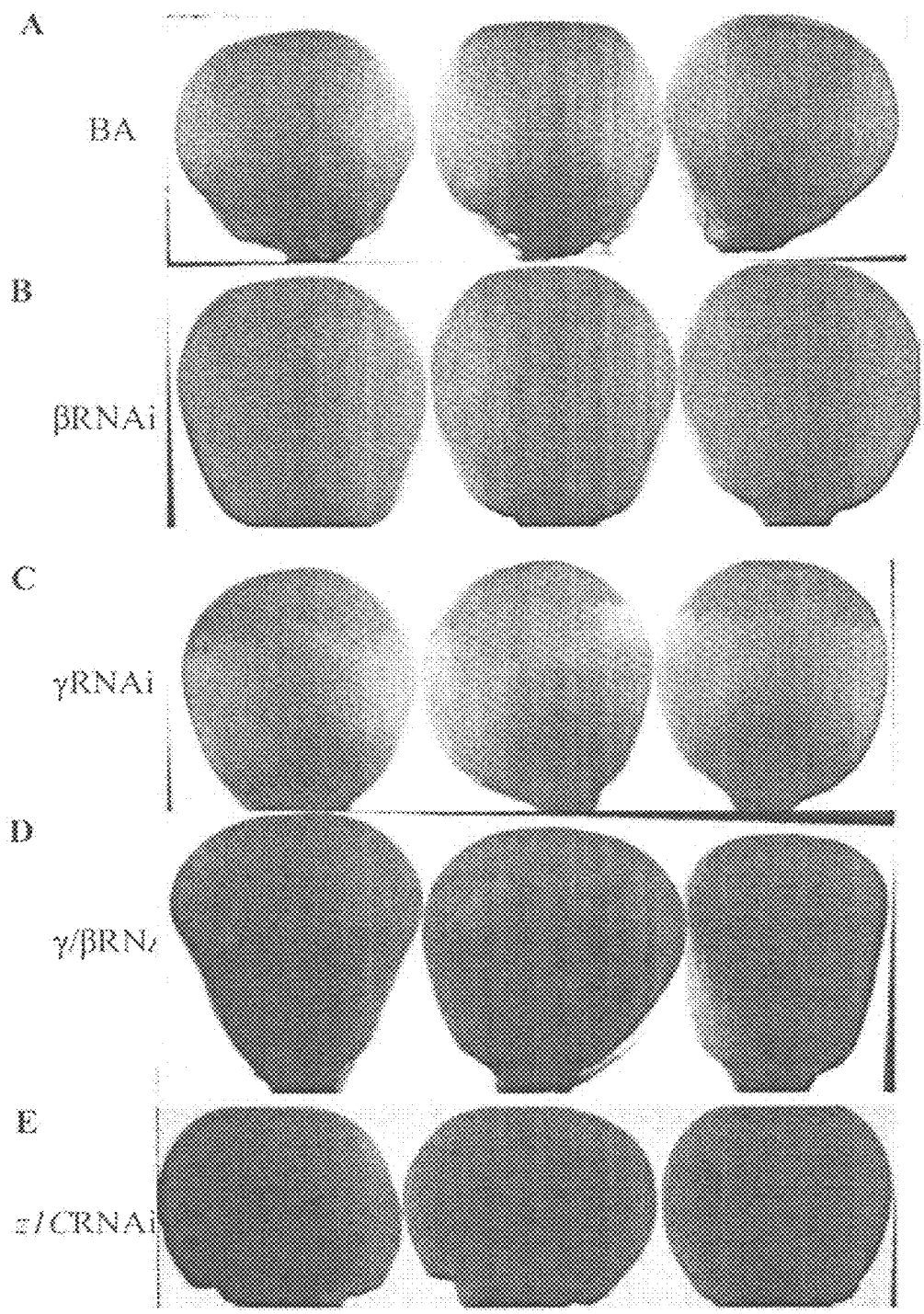
FIG. 6: Kernel opacity of the RNAi mutants. (A) Non-transgenic hybrid of B×A lines. (B) βRNAi. (C) γRNAi. (D) β/γRNAi. (E) z1CRNAi. Vector maps of these constructs are provided in FIGS. 6F and 6G.
Figure 6F:
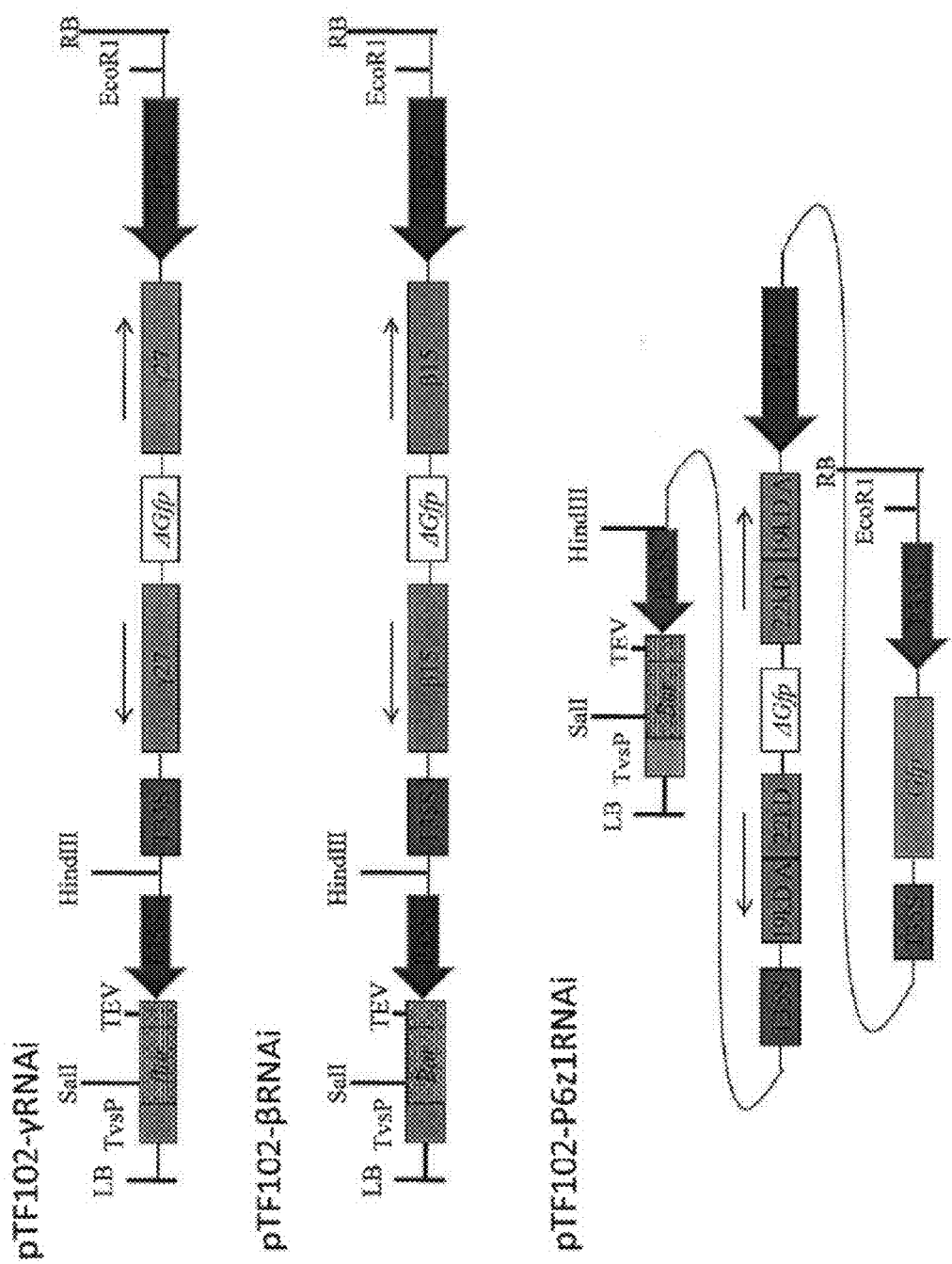
Figure 6G:
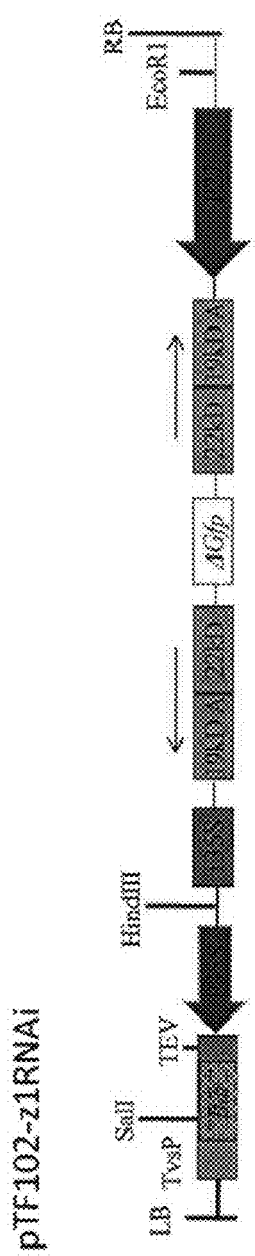
Figure 7:
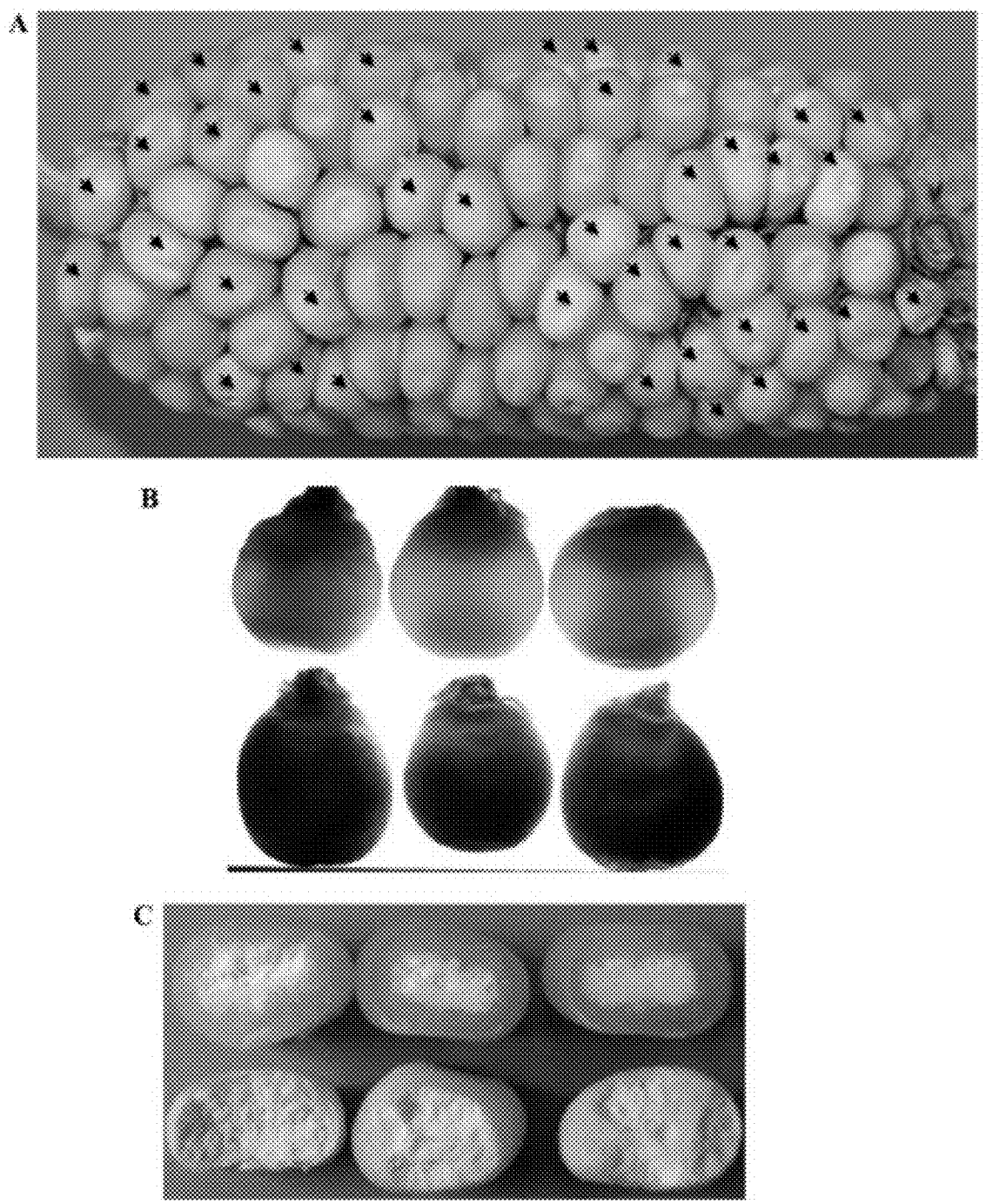
FIG. 7: Ear and kernel phenotype resulting from CM105Mo2×Mo2/+; o2/o2; γRNAi/+. (A) Ear phenotype showing 1:1 ratio of vitreous and opaque kernels; opaque kernels are indicated by arrows. (B) Three representative vitreous and opaque kernels from the ear photographed on the light box. (C) Three representative vitreous and opaque kernels from the ear were truncated and photographed under the natural light.

The breeding of QPM lines can easily be monitored by kernel phenotype because modifiers restore the translucency of the kernel that is lost in opaque mutants. In the progeny of CM105Mo2×(W64Ao2×γRNAi/+), kernels with the genotype Mo2/+; o2/o2; γRNAi/+ are not only sharply reduced in α-zein, but also in γ-zeins. The 27-kDa γ-zein locus is linked to one of the QTLs for endosperm vitreousness (24) and is associated with increased 27-kDa γ-zein expression (21). It is not known if a mutation in the 27-kDa γ-zeingene or promoter is the QTL itself or if its expression is affected by another gene, which is itself the QTL. In either case, the question is raised as to whether the restoration of vitreousness depends on a threshold level of γ-zeins. If enhanced γ-zein levels allow endosperm modification either acting independently or in concert with other o2 modifiers, its loss should result in reappearance of the soft o2 phenotype. Indeed, the resulting ear exhibited a 1:3 segregation of opaque and vitreous kernel phenotypes, instead of the 100% vitreous, as would be expected if 27-kDa γ-zein was not necessary for modification (FIG. 5). Progeny kernels carrying the dominant RNAi construct were totally opaque and contained negligible hard endosperm compared with normal and QPM kernels (FIG. 5), although normal kernels with only the γRNAi showed no or only slight opacity in the crown area (FIG. 6C) (9). When the kernels with the genotype Mo2/+; o2/o2; γRNAi/+ were backcrossed with CM105Mo2, progeny exhibited 1:1 segregation of opaque and vitreous kernel phenotypes (FIG. 7). In such cases, half of the progeny should be homozygous for the 27-kDa γ-zein locus, the major QTL for endosperm modification in QPM. If heterozygosity of this modifier would be insufficient for a vitreous phenotype, one would expect only a 3:1 segregation because only a quarter of the progeny would be both γRNAi and homozygous for the modifier. These data confirm the link between the QPM phenotype and γ-zein levels in endosperm. There is a good correlation between transmission electron microscopy observations of PBs and kernel phenotypes.

Triple Stack of z1CRNAi, γRNAi, and βRNAiTransgenes.

It has been shown that O2 regulates more genes than just the 22-kDa α- and β-zeins (39, 40). Furthermore, the QPM phenotype comprises several QTLs, which make quantitative contributions (24). It is therefore conceivable that other factors might be responsible for the disintegration of the subcellular structure of PBs and starch granules in addition to or instead of the regulation of γ- and α-zein gene expression. To exclude these potential pleiotropic effects, a triple stack of z1CRNAi, γRNAi, and βRNAitransgenes was created (FIG. 8) by reciprocal crosses between a homozygous z1CRNAi transgenic plant (16) and a plant heterozygous for γRNAi and βRNAi (9).

Figure 8:
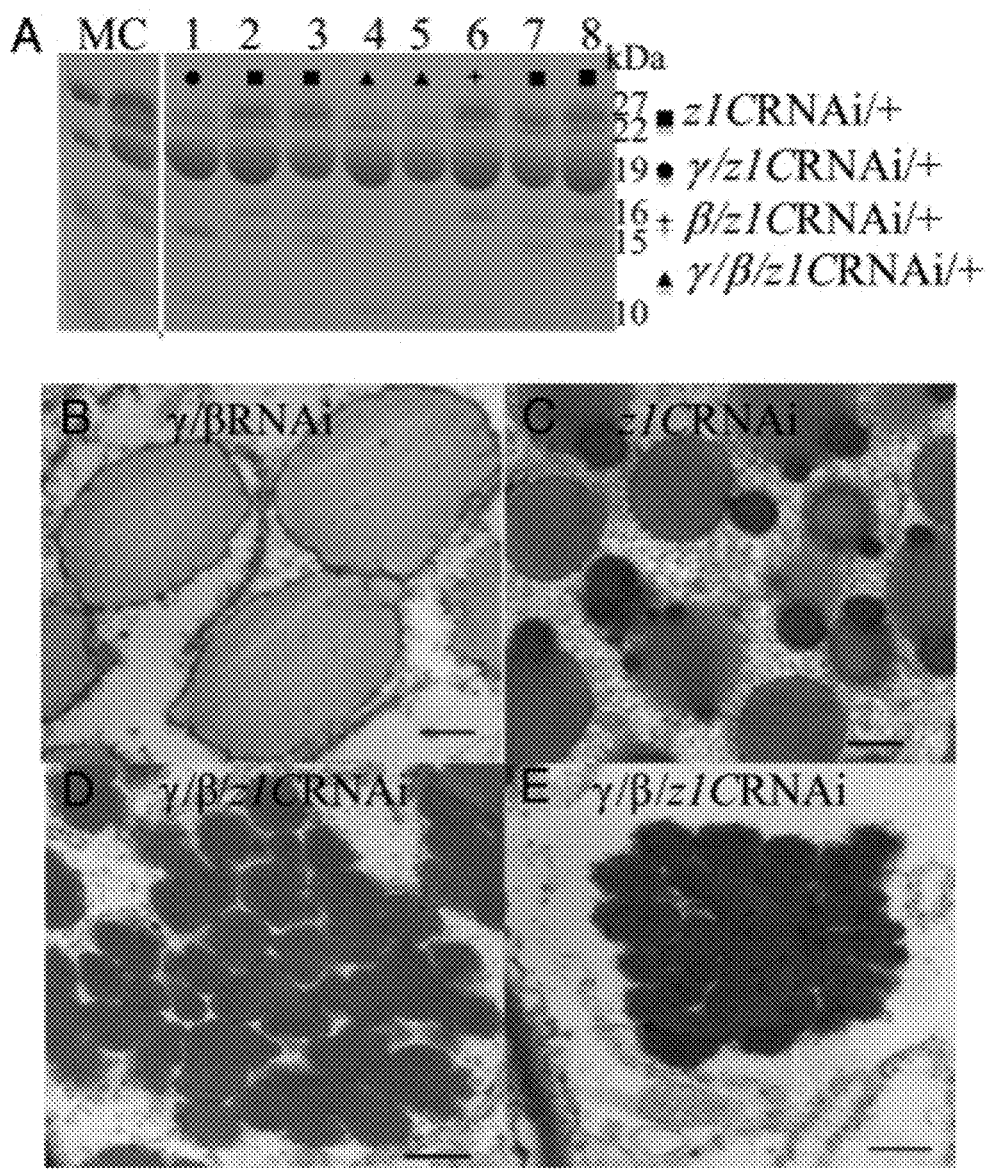
FIG. 8: Protein accumulation analysis of the γ/βRNAi, z1CRNAi and their triple-stack (z1CRNAi used as pollen) and transmission electron micrographs of their protein bodies. (A) Eight kernels dissected from the cross of γ/β RNAi×z1CRNAi at 18 DAP were analyzed. C, nontransgenic hybrid seed of B and A lines as a control. M, protein markers from top to bottom being 25, 20, 15, and 10 kDa. The slice of protein markers and control run in a different gel was composited with the samples, as indicated by a white line. Total zein loaded in each lane was equal to 500 μg of fresh endosperm at 18 DAP. The size for each band is indicated in the "kDa" column. (B-E) Transmission electron micrographs of protein bodies in γ/β RNAi stack (B), z1CRNAi (C), and the stack of γ/β RNAi and z1CRNAi (D and E). (Scale bars, 500 nm.)
Figure 9:
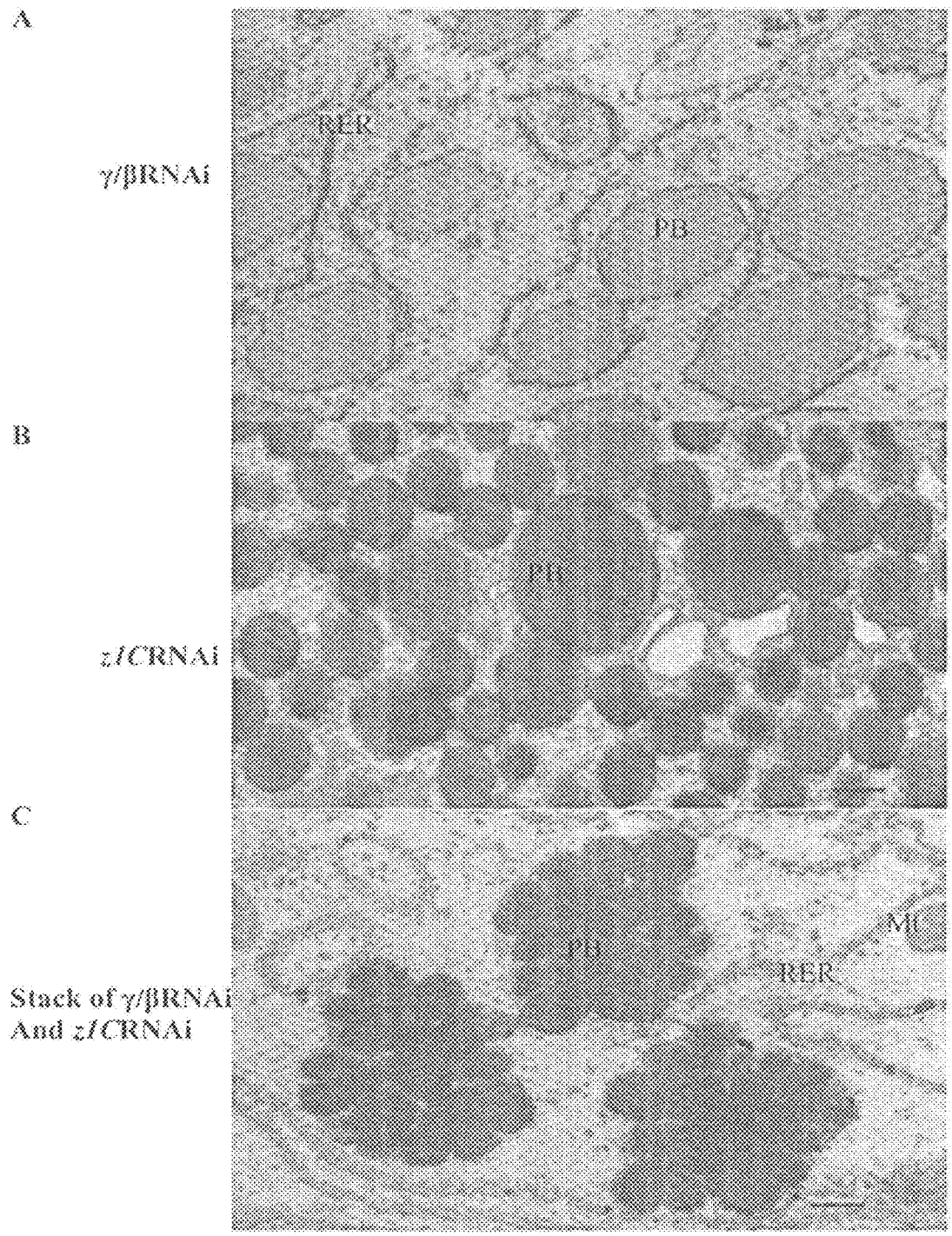
FIG. 9: Transmission electron micrographs of protein bodies in different RNAi mutants with wider field view at 18 d after pollination. (A) γ/βRNAi (B) z1CRNAi. (C) Stack of γ/βRNAi and z1CRNAi. (Scale bars, 500 nm.) Mt, mitochondria; PB, protein body; RER, rough endoplasmic reticulum.

Both parental lines were used as references for SDS/PAGE and transmission electron microscopic analysis (FIGS. 8 A-C and FIGS. 9 A and B). At 18 DAP, eight immature kernels were dissected for extraction of total zeins. A non-transgenic Hi II hybrid seed of B×A lines was used as a control. As expected, all kernels exhibited reduced 22-kDa α-zein levels. Other zeins were not affected, indicating the highly specific action of RNAi (FIG. 8A). Kernels 2, 3, 7, and 8 represented the genotype z1CRNAi/+, with only the 22-kDa α-zeins reduced; kernels 4 and 5 represented the genotype z1CRNAi/+; γRNAi/+; βRNAi/+, with not only the 22-kDa α-zein but also γ- and β-zeins reduced; kernels 1 and 6 represented the genotype z1CRNAi/+; γRNAi/+ and z1CRNAi/+; βRNAi/+, respectively, both besides substantially losing the 22-kDa α-zeins, the γ-zeins or β-zein being knocked down to barely detectable levels as well (FIG. 8A). As expected, the kernels with the triple stack of the z1CRNAi, γRNAi, and βRNAi showed a full opaque phenotype, similar to kernels with z1CRNAi alone (FIG. 6E) (9, 16, 41), indicating that a significant loss of α-zeins is sufficient to cause kernel opacity alone (FIG. 6E).

Figure 10:
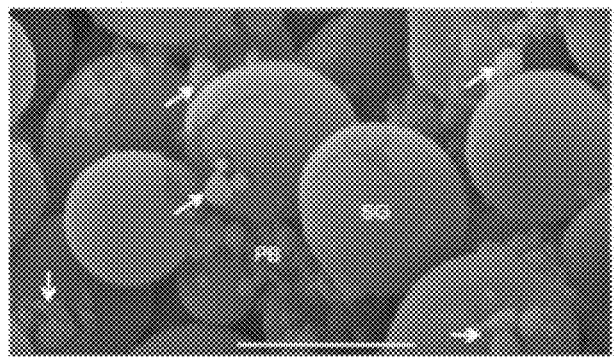
FIG. 10: Scanning electron micrographs of the protein bodies from the triple stack of the z1CRNAi and γ/βRNAi (the z1CRNAi used as pollen) at 18 d after pollination. (Scale bar, 10 μm.) SG, starch granules; PB, protein body. Unseparated PBs are indicated by arrows.
Figure 11:
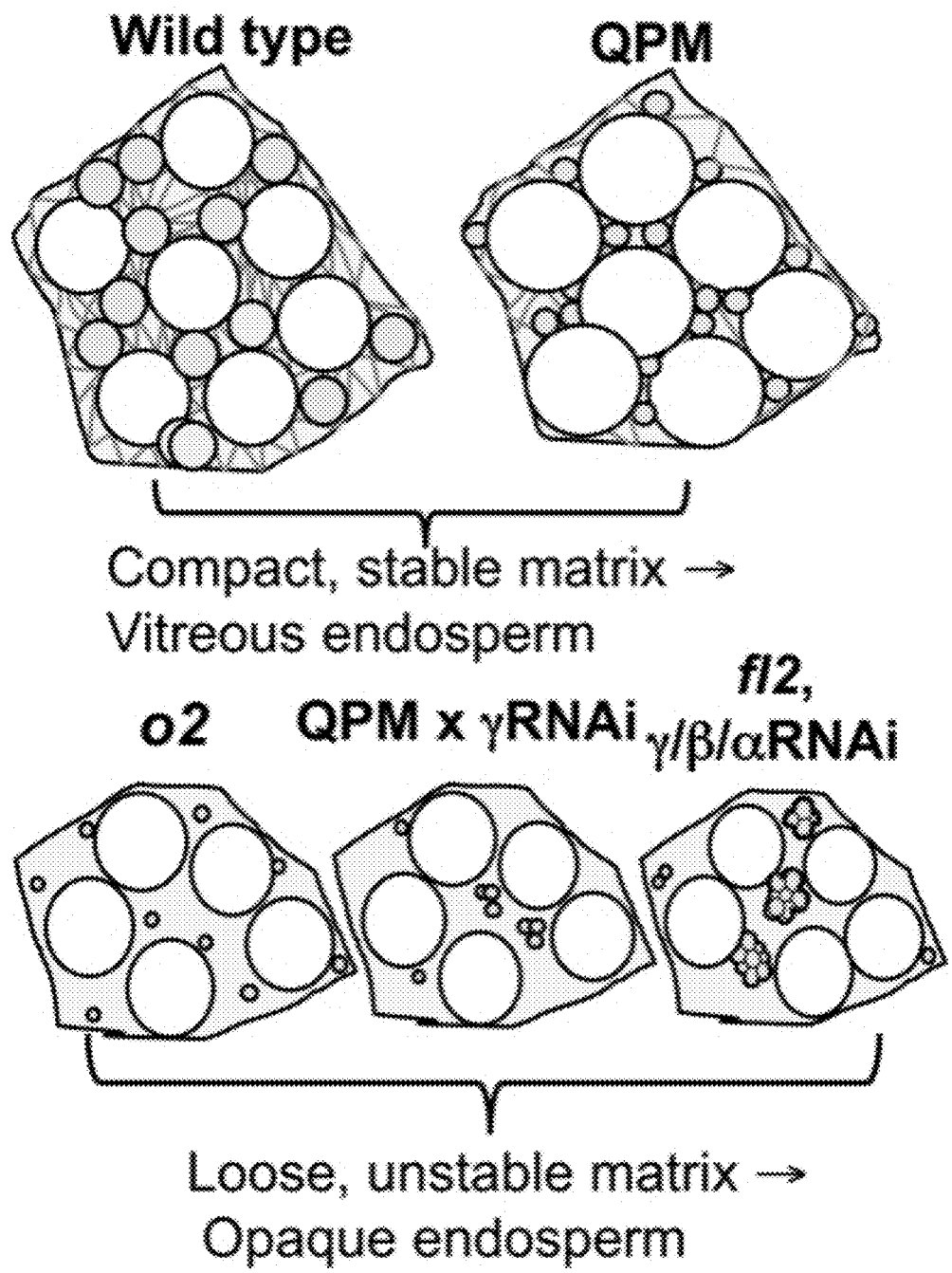
FIG. 11: Model for vitreous endosperm formation in which mid-maturation stage (18 DAP) starchy endosperm cells are depicted. PBs are represented with gray spheres, starch grains with white spheres, and proteinaceous matrix with blue lines. In wild-type and QPM, compact stable matrices give rise to glass-like, vitreous endosperm at maturity. In opaque mutants and dominant RNAi low-zein lines, small, sparse, or lobed unseparated PBs produce loose, unstable matrices, which shatter during desiccation, producing an opaque texture at maturity.

Most PBs in the triple stack of z1CRNAi, γRNAi, and βRNAi had an irregular shape similar to the double stack of βRNAi and γRNAi (FIGS. 8 B, D, and E and FIG. 9 A-C) (9). Moreover, the mature PBs were no longer discrete but consisted of masses that appeared to comprise tens of unseparatedPBs, with diameters considerably larger than the normal 1- to 2-μm size (FIGS. 8 D and E and FIG. 9C). This finding was similar to the observations in the stack of QPM and γRNAi (FIGS. 2 E and F and FIGS. 3 E and F), only more severe Scanning electron microscopy revealed that these PB masses could still interact with starch grains (FIG. 10). Because of the abnormal size and shape of PB masses and their unknown surface characteristics, it seems that interactions with starch grains are not able to contribute to the formation of a vitreous endosperm upon desiccation (FIG. 11).

Mechanism of PB Aggregation.

Undoubtedly, one effect of the γRNAi effect on QPM is to prevent accretion of zeins into normally shaped endoplasmic reticulum-derived PBs. Other mutants with similar clumped PBs always show the opaque endosperm phenotype (9, 11, 12, 14). What could cause this abnormal PB phenotype? Our use of an RNAitransgene permits us to exclude the pleiotropic effects of the conventional trans-acting factors, like O2. Lobing and failed separation of PBs occurs when both Cys-rich (γ- and β-) and Cys-poor (22-kDa α-) zeins were reduced simultaneously, suggesting that the phenotype is associated with a quantitative and qualitative loss of zeins, rather than a reduction only in either the 22-kDa α-zein or γ- and β-zeins (FIGS. 8 B and C and FIGS. 9 A and B). Protein levels alone cannot be the basis for the phenotype because, although both triple-stacked RNAi and o2 have dramatically reduced total zeins, o2 has discrete PBs. The difference is that the γ-zeins reach normal levels in the o2 mutant but are lost in the triple stack. Therefore, lobed and unseparated PB masses occur when both α- and γ-/β-zein classes are reduced to low levels. It is possible that the residual 19-kDa α-zeins in the QPM×RNAi and the α-, β-, and γ-RNAi triple stack prevent PB separation because of the loss of encapsulating γ-zeins, and that their difference in relative severity relates to the amount of residual α-zeins. In comparison, o2 has normal discrete PBs because residual α-zeins are encapsulated in γ-zeins. This explanation for disrupted PB separation is summarized in Table 2.

TABLE 2

Effect of zein disruptions on protein-body morphology

| Genotype | Zeins present | Zein interactions | Phenotype |
|---|---|---|---|
| o2 | Low levels of 19- and 22-α; normal γ | Residual α are encased in γ | No PB lobing |
| QPM γRNAi | Low levels of 19- and 22-α; low γ | Residual α are not encased in γ | Moderate PB lobing |
| Triple stack (22-α, -γ, and -β RNAi) | Moderate 19- and low 22-α; low γ | Lots of 19 α are not encased in γ | More severe PB lobing |

Interestingly, the morphology and organization of PBs in this triple stack is reminiscent of fl2, where protein-body separation is also disrupted (34); fl2 is linked to a single 22-kDa zein gene with an amino acid change that prevents processing of the signal peptide, thereby slowing down the deposition of other zeins into PBs. During early PB formation, only γ- and β-zeins are deposited (8), and this explains the variable penetrance of the phenotype in relation to the PB size gradient between the subaleurone layer and the central portion of the endosperm (34). The fused PBs observed in our triple RNAi stack may arise by the same mechanism as in fl2, as both have reduced accumulation of α-zeins, as well as γ- and β-zeins. A common feature of fl2 and the triple stack may be their "out of context" accumulation of α-zeins, where the semi-dominant mutant fl2 α-zein or large amounts of the 19-kDa α-zeins lack the encapsulating 22-kDa α- and γ-zeins. An unknown mutation causes similarly aggregated PBs in a highly digestible sorghum cultivar (42, 43), inviting speculation that it is caused by a semi-dominant kafirin mutation analogous to floury 2.

It has also been shown that PBs in endosperm cells are not randomly distributed but are evenly distributed around starch granules embedded in a protein matrix rich in EF-1α and cytoskeletal elements, such as actin and microtubules (37). Indeed, seed architecture could have evolved to use the cytoskeletal network in the distribution of PBs. If this is the case, the interaction between PBs and the cytoskeleton could depend on an appropriate internal PB structure, which depends on the timely accumulation of the correct proportions of γ-, β-, and α-zeins. In o2 endosperm, this balance is upset both in terms of PB size, shape, and the surrounding protein matrix (FIG. 11). These parameters are only partially restored to wild-type in QPM but result in kernels that are as vitreous as wild-type. In this case, it is possible that the increased 27 kDa γ-zein allows the accumulation of small but numerous PBs that, along with the proteinaceous matrix, participate in a mature endosperm structure whose vitreousness perhaps develops in a somewhat distinct manner from wild-type (FIG. 11). Whether similar or distinct to wild-type endosperm maturation, we are unique in showing that an increase in γ-zein is essential for endosperm modification in QPM.

Example II

Basis and Selection for Quality Protein Maize (QPM)

Quality protein maize (QPM) restored kernel hardness of high lysine o2 soft endosperm, but two needs remained unmet, our knowledge of the molecular basis of o2 modifiers (Mo2) and an accelerated conversion of any germplasm to facilitate its broader application at reasonable cost. To explore these two needs, a series of RNAi transgenes, blocking γ-, β- and α-zein synthesis, were generated.

Previous studies showed that one of the QTLs was linked to the 27-kDa γ-zein locus on chromosome 7S. Indeed, QPM lines had 2- to 3-fold higher levels of 27-kDa γ-zein. Moreover, it could be shown that elimination of γ-zeins disrupted endosperm modification by Mo2s, indicating their hypostasis to γ-zeins. Abnormalities in protein body structure and their interaction with starch granules in the F1 with Mo2/+; o2/o2; γRNAi/+ genotype suggested that γ-zeins were essential for restoring protein body density and starch grain interaction in QPM. It appears that gamma zeinRNAi acts dominantly over QPM modifiers conferring undesirable traits onto resulting kernels. See FIG. 7. The data presented in the present example reveal that desirable QPM modifiers act in a dominant fashion in plants where alpha zein has been down modulated via RNAi. Accordingly, down modulation of these two zeins have different impacts on the generation of QPM.

Figure 12:
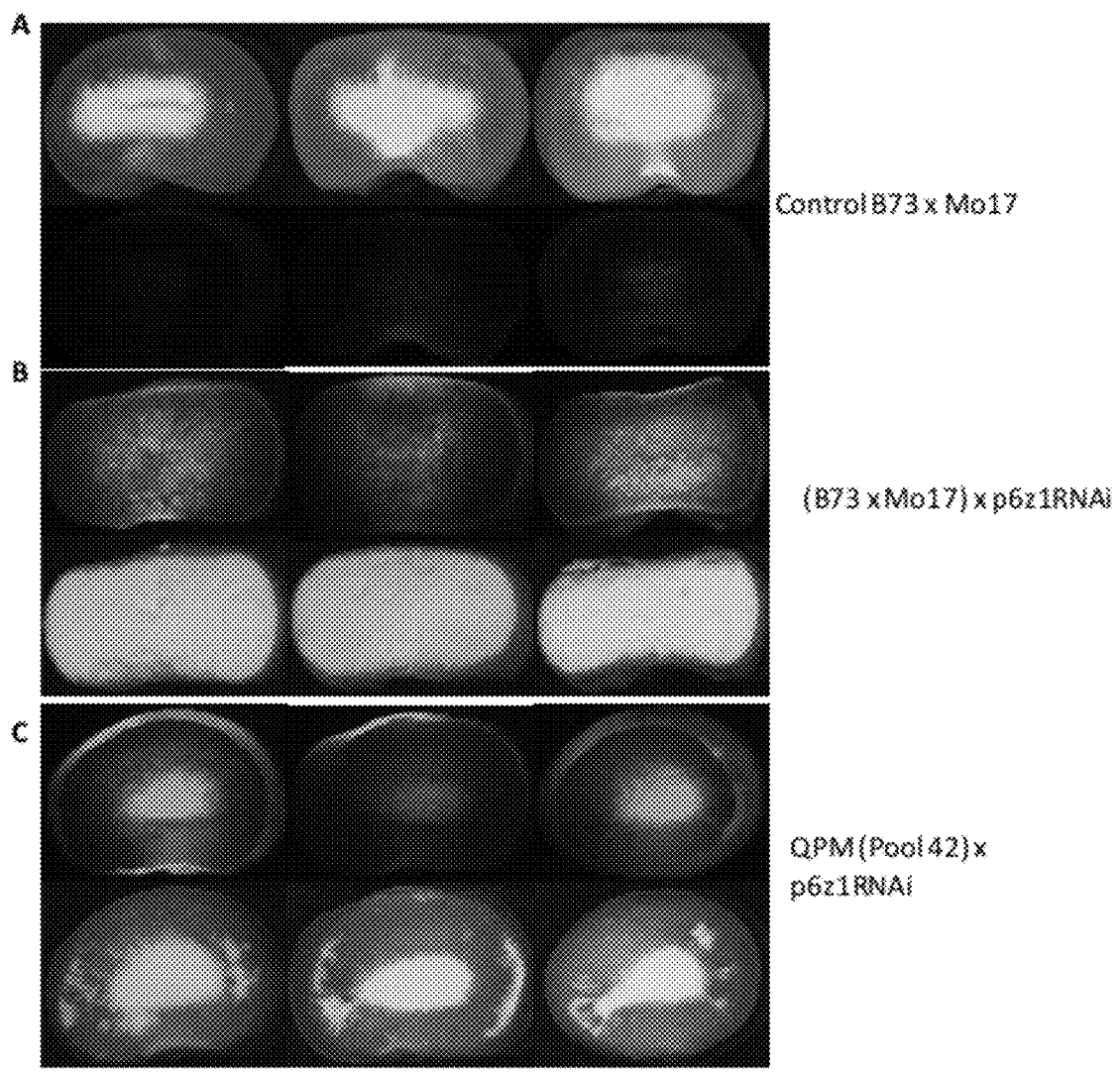
FIG. 12: Illustration of a synthetic QPM. Panel A shows progeny kernels (cut) from a cross between B73×Mol7. Top row shows kernels without fluorescent staining while the lower one does. Lower row, non-stained kernels produce the typical vitreous kernel of maize and are non-fluorescent. Panel B: The (B73×Mol7) hybrid is crossed with p6z1RNAi.

As described at length above, for conversion of elite lines into QPM, breeders first have to make both parental lines homozygous for o2, and then convert them into QPM, respectively. During this process, breeders have to monitor the recessiveness of o2 and the presence of Mo2, a lengthy process that discourages the spread of the benefits of QPM to consumers. On the basis of the hypostasis of γ-zeins, we developed a universal and accelerated QPM conversion approach. Instead of using the recessive o2 mutation, we were using an RNAi construct against both 22- and 19-kDa zeins, but linked to the visible GFP marker gene. Indeed, when such green and non-vitreous phenotypes were crossed with QPM lines, Mo2 produces a vitreous green kernel, illustrating that high-lysine and kernel hardness can be selected in a dominant fashion. Furthermore, it then becomes easy to replace the transgene either with o2 again or a transgene without the GFP. See FIGS. 12 and 13.

REFERENCES FOR EXAMPLES I AND II

1. Moose S P, Dudley J W, Rocheford T R. Maize selection passes the century mark: A unique resource for 21st century genomics. Trends Plant Sci. 2004; 9:358-364.
2. Esen A. A proposed nomenclature for the alcohol-soluble proteins (zeins) of maize (Zea mays L.) J Cereal Sci. 1987; 5:117-128.
3. Osborne T B. Process of extracting zein. 1891 U.S. Pat. No. 456,773.
4. Sodek L, Wilson C M Amino acid composition of proteins isolated from normal, opaque-2, and floury-2 corn endosperms by a modified Osborne procedure. J Agric Food Chem. 1971; 19:1144-1150.
5. Xu J H, Messing J. Organization of the prolamin gene family provides insight into the evolution of the maize genome and gene duplications in grass species. Proc Natl Acad Sci USA. 2008; 105:14330-14335.
6. Woo Y M, Hu D W, Larkins B A, Jung R. Genomics analysis of genes expressed in maize endosperm identifies novel seed proteins and clarifies patterns of zein gene expression. Plant Cell. 2001; 13:2297-2317.
7. Larkins B A, Hurkman W J. Synthesis and deposition of zein in protein bodies of maize endosperm. Plant Physiol. 1978; 62:256-263.
8. Lending C R, Larkins B A. Changes in the zein composition of protein bodies during maize endosperm development. Plant Cell. 1989; 1:1011-1023.
9. Wu Y, Messing J. RNA interference-mediated change in protein body morphology and seed opacity through loss of different zein proteins. Plant Physiol. 2010; 153:337-347.
10. Holding D R, et al. The maize floury1 gene encodes a novel endoplasmic reticulum protein involved in zein protein body formation. Plant Cell. 2007; 19:2569-2582.
11. Kim C S, et al. A defective signal peptide in a 19-1W alpha-zein protein causes the unfolded protein response and an opaque endosperm phenotype in the maize De*-B30 mutant. Plant Physiol. 2004; 134:380-387.
12. Coleman C E, et al. Expression of a mutant alpha-zein creates the floury2 phenotype in transgenic maize. Proc Natl Acad Sci USA. 1997; 94:7094-7097.
13. Coleman C E, Lopes M A, Gillikin J W, Boston R S, Larkins B A. A defective signal peptide in the maize high-lysine mutant floury 2. Proc Natl Acad Sci USA. 1995; 92:6828-6831.

14. Kim C S, et al. The maize Mucronate mutation is a deletion in the 16-kDa gamma-zein gene that induces the unfolded protein response. Plant J. 2006; 48:440-451.
15. Mertz E T, Bates L S, Nelson O E. Mutant gene that changes protein composition and increases lysine content of maize endosperm. Science. 1964; 145:279-280.
16. Segal G, Song R, Messing J. A new opaque variant of maize by a single dominant RNA-interference-inducing transgene. Genetics. 2003; 165:387-397.
17. Osborne T B, Mendel L B. Nutritional properties of proteins of the maize kernel. J Biol Chem. 1914; 18(1):1-16.
18. Osborne T B, Mendel L B. Amino-acids in nutrition and growth. J Biol Chem. 1914; 17:325-349.
19. Emerson R A, Beadle G E, Fraser A C. A summary of linkage studies in maize. Cornell University Agricultural Experiment Station Memoir. 1935; 180:1-83.
20. Vasal S K, Villegas E, Bjarnason M, Gelaw B, Goertz P. Genetic modifiers and breeding strategies in developing hard endosperm opaque 2 materials. In: Prollmer M G, Phillips R H, editors. Improvement of Quality Traits of Maize for Grain and Silage Use. London: MartinusNijhoff; 1980. pp. 37-73.
21. Geetha K B, Lending C R, Lopes M A, Wallace J C, Larkins B A. Opaque-2 modifiers increase gamma-zein synthesis and alter its spatial distribution in maize endosperm. Plant Cell. 1991; 3:1207-1219.
22. Schmidt R J, Ketudat M, Aukerman M J, Hoschek G. Opaque-2 is a transcriptional activator that recognizes a specific target site in 22-1W zein genes. Plant Cell. 1992; 4:689-700.
23. Ueda T, et al. Mutations of the 22- and 27-kD zeinpromotersaffecttransactivation by the Opaque-2 protein. Plant Cell. 1992; 4:701-709.
24. Holding D R, et al. Genetic analysis of opaque2 modifier loci in quality protein maize. Theor Appl Genet. 2008; 117:157-170.
25. Dannenhoffer J M, Bostwick D E, Or E, Larkins B A. Opaque-15, a maize mutation with properties of a defective opaque-2 modifier. Proc Natl Acad Sci USA. 1995; 92:1931-1935.
26. Thompson G A, Larkins B A. Characterization of zein genes and their regulation in maize endosperm. In: Freeling M, Walbot V, editors. The Maize Handbook. New York: Springer-Verlag; 1994. pp. 639-647.
27. Holding D R, Larkins B A. Zein storage proteins. In: Kriz A L, Larkins B A, editors. Molecular Genetic Approaches to Maize Improvement. Berlin: Springer; 2009. pp. 269-286.
28. Cord Neto G, et al. The involvement of Opaque 2 on beta-prolamin gene regulation in maize and Coix suggests a more general role for this transcriptional activator. Plant Mol Biol. 1995; 27:1015-1029.
29. Or E, Boyer S K, Larkins B A. Opaque2 modifiers act post-transcriptionally and in a polar manner on gamma-zein gene expression in maize endosperm. Plant Cell. 1993; 5:1599-1609.
30. Wu Y, Goettel W, Messing J. Non-Mendelian regulation and allelic variation of methionine-rich delta-zein genes in maize. Theor Appl Genet. 2009; 119:721-731.
31. Gibbon B C, Wang X, Larkins B A. Altered starch structure is associated with endosperm modification in Quality Protein Maize. Proc Natl Acad Sci USA. 2003; 100:15329-15334.
32. Wang X, Woo Y M, Kim C S, Larkins B A. Quantitative trait locus mapping of loci influencing elongation factor 1alpha content in maize endosperm. Plant Physiol. 2001; 125:1271-1282.
33. Wolf M J, Khoo U, Seckinger H L. Subcellular structure of endosperm protein in high-lysine and normal corn. Science. 1967; 157:556-557.
34. Lending C R, Larkins B A. Effect of the floury-2 locus on protein body formation during maize endosperm development.Protoplasma. 1992; 171:123-133.
35. Zhang F, Boston R S. Increases in binding protein (BiP) accompany changes in protein body morphology in three high-lysine mutants of maize. Protoplasma. 1992; 171: 142-152.
36. Duvick D N. Protein granules of maize endosperm cells. Cereal Chem. 1961; 38:374-385.
37. Clore A M, Dannenhoffer J M, Larkins B A. EF-1[alpha] is associated with a cytoskeletal network surrounding protein bodies in maize endosperm cells. Plant Cell. 1996; 8:2003-2014.
38. Balconi C, Berardo C, Reali A, Motto M. Variation in protein fractions and nitrgen metabolism of developing normal and opaque endosperm mutants of maize. Maydica. 1998; 43:195-203.
39. Hunter B G, et al. Maize opaque endosperm mutations create extensive changes in patterns of gene expression. Plant Cell. 2002; 14:2591-2612.
40. Bass H W, Webster C, OBrian G R, Roberts J K, Boston R S. A maize ribosome-inactivating protein is controlled by the transcriptional activator Opaque-2. Plant Cell. 1992; 4:225-234.
41. Huang S, et al. Improving nutritional quality of maize proteins by expressing sense and antisense zein genes. J Agric Food Chem. 2004; 52:1958-1964.
42. Oria M P, Hamaker B R, Axtell J D, Huang C P. A highly digestible sorghum mutant cultivar exhibits a unique folded structure of endosperm protein bodies. Proc Natl Acad Sci USA. 2000; 97:5065-5070.
43. Tesso T, Hamaker B R, Ejeta G. Sorghum protein digestibility is affected by dosage of mutant alleles in endosperm cells. Plant Breeding. 2008; 127:579-586.
44. Burr B, Burr F A. Zein synthesis in maize endosperm by polyribosomes attached to protein bodies. Proc Natl Acad Sci USA. 1976; 73:515-519.

Example III

RNA Interference can Rebalance Nitrogen Sink of Maize Seeds without Loss of Hard Endosperm As explained in the previous examples, Maize (*Zea mays*), commonly known as corn, produces the highest yield among the major crops in the world. Although its yields are nearly four times higher than soybean (*Glycine max*), maize and other cereals are much less nutritious in terms of protein content and amino acid composition. Typical yellow dent maize contains 10% protein(1), of which the essential amino acid lysine is around 2% (2), whereas soybean has 35% protein with sufficient levels of lysine. Therefore, maize meal is always supplemented with soybean in feed to meet the protein and lysine needs of livestock.

The following materials and methods are provided to facilitate the practice of Example III.

Genetic Stocks

The P6z1RNAi transgenic plant has been described above. The P6z1RNAi transgenic plant was then backcrossed to B73 for two generations (FIG. 16A), which consistently showed 1:1 ratio of vitreous (non-green) and opaque (green) seeds segregating in each generation. The four Illinois Protein Strains (IHP, IRHP, ILP and IRLP) were obtained from Dr. Stephen Moose of the University of Illinois. B73, W64A and W64o2 were from our own stocks.

Total Zein and Non-Zein Protein Extraction, Protein and Amino Acid Composition Analysis For zein extraction, the dry kernels were wrapped individually in two layers of thick aluminum foil and crushed into fine flour by a heavy hammer. For each kernel, only 50 mg of flour was transferred to a 2 ml Eppendorf tube, then mixed and vortexed with 400 of 70% ethanol/2% 2-mercaptoethanol (v/v), then kept on the bench at room temperature overnight; the mixture was centrifuged at 13,000 rpm in a bench top microfuge for 10 min, then 100 µl of the supernatant liquid was transferred to a new tube; 100 of 10% SDS was added to the extract, the mixture was dried by vacuum and resuspended in 100 µl of distilled water.

For non-zein extraction, the supernatant from above was discarded. Solids remaining in the tube were resuspended with zein extraction buffer to completely remove the zeins from other proteins. This step was repeated for 3 times. At last, the residual solids were suspended in 400 of non-zein extraction buffer (12.5 mM sodium borate, 5% SDS and 2% 2-mercaptoethanol (vol/vol)). The mixture was kept at 37° C. for two hours and vortexed several times in this period. The mixture was centrifuged at 13,000 rpm for 10 min, and then 100 µl of the non-zein supernatant was transferred to a new tube. 4 µl (equal to 500 µg of floury) of each sample was analyzed with 15% SDS-PAGE gel.

About 20 g of mature seeds were ground to fine flour. The protein and amino acid composition analysis was conducted by the New Jersey Feed Laboratory, Inc., Trenton, N.J., USA.

Incandescent and Fluorescent Light Dissection Microscopy

Kernels were truncated and scoped under incandescent and fluorescent light dissection microscopes, respectively (WILD M3 and Leica MZ16 F).

Results

To improve protein concentration in maize, a well-known long-term selection-experiment was initiated in 1896 by C. G. Hopkins at the University of Illinois(3) and has lasted for more than a century(4-6), yielding four strains, Illinois High Protein (IHP), Low protein (ILP), Reverse High protein (IRHP) and Reverse Low Protein (IRLP). Introgressed QTLs are capable of raising the protein concentration in IHP more than twice that in normal maize, with the most increased fraction being the alcohol-soluble proteins or prolamins. Seed storage proteins are classified into albumins, globulins, glutelins, and prolamins based on their solubilities in different solvents(7). The major storage proteins in maize are prolamins, known as zeins, amounting to more than 60% of total protein. However, soon after the initiation of the Illinois long-term selection experiment in 1914, zein was shown to contain no lysine(8). Because more than 60% of the zeins are almost lysine-free, the overall lysine in maize seed is reduced to a level as low as 2%. Therefore, despite its higher protein content, IHP is of little value for feeding monogastric animals. Indeed, the lysine content of total protein is even lower than that in normal maize because of the proportion of increased zeins.

Although QPM has more balanced amino acid composition than normal maize, its total protein level is much lower than that of soybeans. It seems that the three critical traits of valuable maize germplasm, high protein, high lysine, and hard endosperm remained an ever-lasting breeding challenge that could not be overcome all at once.

The vitreousness of IRHP is between that of IHP, IRLP and ILP (FIG. 14A). IHP and IRLP kernels are translucent and vitreous, whereas ILP kernels are opaque and starchy. To correlate vitreousness with protein content, zeins and non-zeins were fractionated by different extraction solvents and separated electrophoretically by SDS-PAGE (FIG. 14A). Consistent with their kernel phenotypes, IHP and IRLP accumulated the highest and second highest amount of zeins, respectively, with the most prominent bands being the 22- and 19-kDa α-zeins. They are followed by B73, IRHP and ILP in respect to zein accumulation. Interestingly, non-zein protein accumulation from highest to lowest is also in the same order: IHP>IRLP>B73>IRHP>ILP. Apparently, the long-term breeding-program accumulated QTLs in IHP that not only increased zeins but also non-zein proteins, suggesting a more general mechanism of controlling total seed protein content. Because the absolute lysine level ($lysine_{ab}$) relates to the proportion of non-zeins in seeds, the contribution of $lysine_{ab}$ is expected to be proportional to non-zeins. Indeed, IHP contains the highest level of lysine with 0.36%, while ILP the lowest with only 0.2% (Table 3). On the contrary, the relative level of lysine ($lysine_{rel}$), which is of nutritional value, is calculated as a percentage of lysine in total protein, directly proportional to the percentage non-zeins in total protein. Therefore, it was not unexpected that ILP have the highest $lysine_{rel}$ (4.35%) level and IHP the lowest (1.47%) (Table 3). However, ILP and IRHP are not suitable choices from a commercial point of view because their total protein concentration is too low, requiring soybean supplementation (Table 3), definitely compromising their nutritional potential. Furthermore, ILP and IRHP are opaque and semi-opaque, indicators for soft kernel texture (FIG. 14A).

Traits of high protein, high lysine, and hard endosperm seem to exclude each other in maize. While higher amounts of zeins increase kernel vitreousness (FIG. 14A), they also decrease the $lysine_{rel}$ at the same time, because $lysine_{rel}$ is inversely proportional to the percentage of zeins of total protein. QPM overcame two of the three traits, producing high lysine and hard kernel properties. However, current QPM germplasms developed at CYMMIT and in South Africa, contain just around 9% protein, which is not comparable to IHP or soybeans(11).

TABLE 3

Protein and amino acid Composition analysis of four Illinois Protein Strains (IHP, IRHP, ILP and IRLP) and B73

| Amino acids | IHP | | IRHP | | ILP | | IRLP | | B73 | |
|---|---|---|---|---|---|---|---|---|---|---|
| | $AA_{ab}$ | $AA_{rel}$ | $AA_{ab}$ | $AA_{rel}$ | $AA_{ab}$ | $AA_{rel}$ | $AA_{ab}$ | $AA_{rel}$ | $AA_{ab}$ | $AA_{rel}$ |
| Lysine | 0.36% | 1.47% | 0.28% | 4.12% | 0.20% | 4.35% | 0.32% | 2.05% | 0.31% | 2.54% |
| Phenylalanine | 1.24% | 5.06% | 0.34% | 5.00% | 0.18% | 3.91% | 0.90% | 5.77% | 0.63% | 5.16% |
| Leucine | 3.85% | 15.71% | 0.75% | 11.03% | 0.41% | 8.91% | 2.35% | 15.06% | 1.65% | 13.52% |
| Isoleucine | 0.50% | 2.04% | 0.21% | 3.09% | 0.11% | 2.39% | 0.50% | 3.21% | 0.40% | 3.28% |
| Threonine | 0.65% | 2.65% | 0.27% | 3.97% | 0.17% | 3.70% | 0.50% | 3.21% | 0.41% | 3.36% |
| Valine | 0.73% | 2.98% | 0.32% | 4.71% | 0.16% | 3.48% | 0.59% | 3.78% | 0.48% | 3.93% |
| Histidine | 0.55% | 2.24% | 0.22% | 3.24% | 0.12% | 2.61% | 0.41% | 2.63% | 0.37% | 3.03% |
| Arginine | 0.70% | 2.86% | 0.32% | 4.71% | 0.22% | 4.78% | 0.59% | 3.78% | 0.54% | 4.43% |
| Glycine | 0.60% | 2.45% | 0.34% | 5.00% | 0.22% | 4.78% | 0.46% | 2.95% | 0.49% | 4.02% |
| Aspartic acid | 1.63% | 6.65% | 0.46% | 6.76% | 0.37% | 8.04% | 0.95% | 6.09% | 0.74% | 6.07% |

TABLE 3-continued

Protein and amino acid Composition analysis of four Illinois Protein Strains (IHP, IRHP, ILP and IRLP) and B73

|  | IHP | | IRHP | | ILP | | IRLP | | B73 | |
| --- | --- | --- | --- | --- | --- | --- | --- | --- | --- | --- |
| Amino acids | $AA_{ab}$ | $AA_{rel}$ | $AA_{ab}$ | $AA_{rel}$ | $AA_{ab}$ | $AA_{rel}$ | $AA_{ab}$ | $AA_{rel}$ | $AA_{ab}$ | $AA_{rel}$ |
| Serine | 1.28% | 5.22% | 0.35% | 5.15% | 0.22% | 4.78% | 0.79% | 5.06% | 0.60% | 4.92% |
| Glutamic acid | 5.23% | 21.35% | 1.10% | 16.18% | 0.65% | 14.13% | 3.04% | 19.49% | 2.26% | 18.52% |
| Proline | 2.08% | 8.49% | 0.59% | 8.68% | 0.34% | 7.39% | 1.33% | 8.53% | 1.15% | 9.43% |
| Hydroxyproline | 0.02% | 0.08% | 0.03% | 0.44% | 0.02% | 0.43% | 0.04% | 0.26% | 0.03% | 0.25% |
| Alanine | 2.26% | 9.22% | 0.53% | 7.79% | 0.33% | 7.17% | 1.41% | 9.04% | 0.94% | 7.70% |
| Tyrosine | 0.93% | 3.80% | 0.24% | 3.53% | 0.12% | 2.61% | 0.53% | 3.40% | 0.45% | 3.69% |
| Total protein | 24.50% | | 6.80% | | 4.60% | | 15.60% | | 12.20% | |

$AA_{ab}$, absolute level of amino acid calculated by percentage of AA in total cornmeal;
$AA_{rel}$, relative level of amino acid calculated by percentage of AA in total protein.

If we were to increase lysine in IRLP and IHP with a reduction of alpha zeins through RNAi, we would expect to obtain a non-vitreous soft seed as we have previously shown with normal maize(12). On the other hand, we also found that the QPM QTLs were dominant over non-vitreousness caused by an alpha zein RNAi. Perhaps, the QTLs of IRLP and IHP would also be dominant over an alpha zein RNAi. Therefore, we pollinated IRLP and IHP with pollen from B73 containing the transgeneP6z1RNAi because progenies should exhibit high protein traits only when IRLP and IHP were used as female parent(13). In the construct P6z1RNAi, the 22- and 19-KDa α-zeinRNAi was coupled with the visible GFP marker, therefore parental seeds were opaque and "green" in normal maize lines(14). The progenies inheriting the construct were easy to score under a green fluorescent dissection microscope. Six "non-green" and "green" kernels sorted from IRLP×P6z1RNAi/− and IHP×P6z1RNAi/− were extracted for zeins and non-zeins individually and the proteins were also separated with SDS-PAGE (FIGS. 15A and 15B). As expected, the accumulation of α-zeins in the six "green" progenies from IRLP×P6z1RNAi/− was dramatically reduced compared to the six "non-green" progenies. Although protein levels are already high for maize seeds, a rebalancing of protein accumulation still occurred as the accumulation of non-zeins in the six "green" progenies was significantly increased (FIG. 15A). As expected from the previous work, kernel opacity was linked to the expression of GFP (FIG. 16A) and the ear exhibited 1:1 ratio of vitreous and opaque segregation (FIG. 16C). The same was the case, when the line with P6z1RNAi was backcrossed to B73 for two generations (FIG. 16B). Therefore, the QTLs of IRLP were not dominant over P6z1RNAi as hoped for.

The result for IHP was strikingly different. Similar to IRLP×P6z1RNAi/−, six "green" progenies from IHP×P6z1RNAi/− had dramatic decreases in α-zein synthesis compared to their "non-green" counterparts (FIG. 15B). However, whereas IHP and the progenies with genotype IHP/−; −/− accumulated higher levels of α-zeins than IRLP and IRLP/−; −/−, respectively (FIGS. 14B and 15A-B), there was still significant more α-zeins in IHP/−; P6z1RNAi/− than in IRLP/−; P6z1RNAi/−. Like IRLP/−; P6z1RNAi/−, the non-zein fraction in IHP/−; P6z1RNAi/− was dramatically enhanced compared to the progenies with genotype IHP/−; −/−. Moreover, the ratios of zeins and non-zeins in total protein of IHP/−; −/− (64% and 36%, respectively) were shifted to 20% and 80% in IHP/−; P6z1RNAi/− because of RNA interference (FIG. 15C). When the accumulations of zeins and non-zeins were compared between W64A, IHP/−; −/−, W64Ao2 and IHP/−; P6z1RNAi/−, the reduced level of zeins in IHP/−; P6z1RNAi/− was still as high as that in normal W64A (FIG. 15D), although it dropped to two third of zeins compared to genotype IHP/−; (FIGS. 15B and 15C).

The residual amount of alpha zeins is sufficient to produce vitreous kernels in the genotype IHP/−; P6z1RNAi/−. GFP positive kernels of IHP/−; P6z1RNAi/− are, indeed, vitreous (FIG. 16A) and no segregation is seen in the IHP/−; P6z1RNAi/− ear (FIG. 16D). When the transgenic line P6z1RNAi, backcrossed twice to B73, was pollinated either by IHP or IRLP, the resulting ears segregated 1:1 ratio of vitreous and opaque kernels (FIGS. 17A and 17B), confirming that expression of the QTLs of high protein requires maternal transmission. Interestingly, IHP QTLs were dominant over P6z1RNAi, but the QTLs of ILHP were recessive. Therefore, it appears that dominance over P6z1RNAi depended on the amount of alpha zeins produced in absolute amounts and not on total protein accumulation. Furthermore, QTLs affect total protein accumulation rather than zein synthesis alone (FIG. 15B and Table 4). See "RNA interference can rebalance nitrogen sink of maize seeds without loss of hard endosperm". (Wu and Messing, manuscript in preparation.)

The aspect that the QTLs in IHP could enhance both zeins and non-zein proteins is critical, because lysine$_{rel}$ appears to be not affected by the absolute amount of zeins in maize meal, but by the ratio of zeins and non-zeins. Although IHP/−; P6z1RNAi/− still produces higher amount of zeins despite RNA interference compared to W64Ao2, the critical difference is that its non-zein fraction is significantly higher than in W64Ao2 (FIG. 15D). From a perspective of a sink-source relationship of amino acids, QTLs would be dominant and the seeds retain the high protein property. Furthermore, the high non-zein protein content should also lift lysine levels in the seed. Indeed, whereas the total protein level in IHP/−; P6z1RNAi/− (24.7%) was high as in IHP (24.5%) and IHP/−; −/− (26.60%), the lysine$_{rel}$ in IHP/−; P6z1RNAi/− was 3.7%, as balanced as in W64o2 (Table 4). Although the lysine$_{rel}$ in IRLP/−; P6z1RNAi/− was above 4%, the kernels were opaque and its practical application would then require layering the QPM QTLs on top of the high protein QTLs, constituting a major challenge to breeders. Therefore, these results show that the RNAi construct P6z1RNAi can now be used to identify QTLs for high protein, high lysine, and a vitreous hard endosperm, thereby providing superior maize lines that will have a high impact on the cost of food supply worldwide. Indeed, one could use an accelerated breeding strategy as recently proposed for the introgression of QPM QTLs into local germplasm(14).

TABLE 4

Protein and amino acid composition analysis of seeds with genotype IHP/—; —/—,
IHP/—; P6c1RNAi/—, IRLP/—; —/—, IRLP/—; P6z1RNAi/—and W64Ao2

| Amino acids | IHP/—; —/— | | IHP/—; P6c1RNAi/— | | IRLP/—; —/— | | IRLP/—; P6z1RNAi/— | | W64Ao2 | |
|---|---|---|---|---|---|---|---|---|---|---|
| | $AA_{ab}$ | $AA_{rel}$ | $AA_{ab}$ | $AA_{rel}$ | $AA_{ab}$ | $AA_{rel}$ | $AA_{ab}$ | $AA_{rel}$ | $AA_{ab}$ | $AA_{rel}$ |
| Lysine | 0.46% | 1.73% | 0.91% | 3.68% | 0.37% | 2.52% | 0.58% | 4.06% | 0.48% | 3.93% |
| Phenylalanine | 1.44% | 5.41% | 0.99% | 4.01% | 0.76% | 5.17% | 0.60% | 4.20% | 0.54% | 4.43% |
| Leucine | 4.31% | 16.20% | 2.18% | 8.83% | 2.03% | 13.81% | 1.19% | 8.32% | 1.06% | 8.69% |
| isoleucine | 0.65% | 2.44% | 0.55% | 2.23% | 0.45% | 3.06% | 0.43% | 3.01% | 0.27% | 2.21% |
| Threonine | 0.75% | 2.82% | 0.83% | 3.36% | 0.49% | 3.33% | 0.54% | 3.78% | 0.44% | 3.61% |
| Valine | 0.86% | 3.23% | 0.82% | 3.32% | 0.60% | 4.08% | 0.64% | 4.48% | 0.41% | 3.36% |
| Histidine | 0.78% | 2.93% | 0.80% | 3.24% | 0.43% | 2.93% | 0.45% | 3.15% | 0.43% | 3.52% |
| Arginine | 0.85% | 3.20% | 1.27% | 5.14% | 0.59% | 4.01% | 0.80% | 5.59% | 0.67% | 5.49% |
| Glycine | 0.67% | 2.52% | 1.02% | 4.13% | 0.41% | 2.79% | 0.58% | 4.06% | 0.58% | 4.75% |
| Aspartic acid | 1.75% | 6.58% | 3.46% | 14.01% | 1.17% | 7.96% | 4.49% | 10.42% | 1.19% | 9.75% |
| Serine | 1.38% | 5.19% | 1.07% | 4.33% | 0.73% | 4.97% | 0.68% | 4.76% | 0.61% | 5.00% |
| Glutamic acid | 5.71% | 21.47% | 4.20% | 17.00% | 3.10% | 21.09% | 2.71% | 18.95% | 2.21% | 18.11% |
| Proline | 2.31% | 8.68% | 1.65% | 6.68% | 1.19% | 8.10% | 1.09% | 7.62% | 0.98% | 8.03% |
| Hydroxyproline | 0.02% | 0.08% | 0.02% | 0.08% | 0.02% | 0.14% | 0.04% | 0.28% | 0.04% | 0.33% |
| Alanine | 2.37% | 8.91% | 1.67% | 6.76% | 1.38% | 9.39% | 1.10% | 7.69% | 1.02% | 8.36% |
| Tyrosine | 1.04% | 3.91% | 0.76% | 3.08% | 0.52% | 3.54% | 0.44% | 3.08% | 0.38% | 3.11% |
| Total protein | 26.60% | | 24.70% | | 14.70% | | 14.30% | | 12.20% | |

$AA_{ab}$, absolute level of amino acid calculated by percentage of AA to total cornmeal;
$AA_{rel}$, relative level of amino acid calculated by percentage of AA in total protein.

REFERENCES FOR EXAMPLE III

1. S. A. Flint-Garcia, A. L. Bodnar, M. P. Scott, *Theor Appl Genet* 119, 1129 (October, 2009).
2. E. T. Mertz, L. S. Bates, O. E. Nelson, *Science* 145, 279 (Jul. 17, 1964).
3. C. G. Hopkins, *Ill. Agric. Exp. Stn. Bull* 55, 205 (1899).
4. S. P. Moose, J. W. Dudley, T. R. Rocheford, *Trends Plant Sci* 9, 358 (July, 2004).
5. J. W. Dudley, R. J. Lambert, *Plant Breed. Rev.* 24, 79 (2004).
6. J. W. Dudley, *Crop Science* 47 (S3), S20 (2007).
7. T. B. Osborne, *Science* 28, 417 (Oct. 2, 1908).
8. T. B. Osborne, L. B. Mendel, *Journal of Biological Chemistry* 18, 1 (1914).
9. D. R. Holding, B. A. Larkins, Zein storage proteins. In *Molecular Genetic Approaches to Maize Improvement*, Kriz, A. L. and Larkins, B. A., eds (Springer Berlin Heidelberg), pp. 269-286. T. Nagata, H. Lorz, J. M. Widholm, Eds., Biotechnology in Agriculture and Forestry (2009), vol. 63.
10. S. K. Vasal, E. Villegas, M. Bjarnason, B. Gelaw, P. Goertz, Genetic Modifiers and Breeding Strategies in Developing Hard Endosperm opaque 2 Materials. In *Improvement of Quality Traits of Maize for Grain and Silage Use*, Pollmer, W. G., Phipps, R. H., eds (Martinus Nijhoff, London), pp. 37-73. (1980).
11. B. M. Prasanna, S. K. Vasal, B. Kassahun, N. N. Singh, *Current Science* 81(10), 1308 (2001).
12. G. Segal, R. Song, J. Messing, *Genetics* 165, 387 (September, 2003).
13. R. Reggiani, C. Soave, N. Di Fonzo, E. Gentinetta, F. Salamini, *Genet. Agrar.* 39, 221 (1984).
14. Y. Wu, J. Messing, *Genetics*, (Jun. 6, 2011).

While the invention has been described in detail and with reference to specific examples thereof, it will be apparent to one skilled in the art that various changes and modifications can be made therein without departing from the spirit and scope thereof.

What is claimed is:

1. A method for rapid and accelerated breeding of quality protein maize (QPM) comprising:
   a) providing seeds from a plant comprising an RNAi construct which acts in a dominant fashion to down modulate expression of 19 and 22 kDa alpha zeins, said down modulation decreasing the vitreous nature of seeds obtained from said plant, said RNAi construct comprising a nucleic acid encoding a selectable marker and a visible reporter gene, said visible reporter gene facilitating identification of cells comprising said RNAi construct;
   b) propagating said seed from a) and crossing the resulting plant with a QPM plant line;
   c) obtaining seeds from plants resulting from said cross and harvesting those kernels which exhibit an increased kernel vitreousness and the signal produced by the visible reporter gene when compared to seeds in a) thereby providing a dominant selectable phenotype for elevated lysine and rapid selection of QPM, the method comprising crossing plants obtained from the kernels of c) with a non-QPM line thereby promoting introgression of the QPM trait into said non-QPM line further comprising breeding a transgenic plant from the harvested kernels to yield a progeny plant that has an increase in the amount of at least one amino acid as a dominant trait, said method comprising backcrossing said progeny plant to said non-QPM parent containing a traditional o2 mutation to eliminate the RNAi transgene construct.

2. A method for production of improved maize seed comprising:
   a) providing seeds from a plant comprising an RNAi construct which acts in a dominant fashion to down modulate expression of 19 and 22 kDa alpha zeins, said down modulation decreasing the vitreous nature of seeds obtained from said plant, said RNAi construct comprising a nucleic acid encoding a selectable marker and a visible reporter gene; wherein said visible reporter gene is used for identification of transformed seeds;
   b) propagating said seeds which exhibit expression of said visible reporter marker gene from a) and crossing the resulting plant with an Illinois High Protein (IHP) line;
   c) obtaining seeds from plants resulting from said cross and harvesting those kernels which exhibit expression of said visible reporter gene, said seeds exhibiting an increased kernel vitreousness, and elevated protein content when compared to seeds in a) or seeds obtained from an Illinois High Protein line lacking said RNAi construct, wherein said seed have the genotype IHP/–; P6z1RNAi/–.

3. The method of claim 2, wherein said seed from step c) exhibits elevated lysine content.

4. The method of claim 2, wherein said seed from step c) exhibits elevated tryptophan content.

5. The method of claim 2, wherein said seed from step c) exhibits elevated methionine content.

6. The method of claim 2, wherein said visible reporter gene is green fluorescent protein.

7. The method of claim 2, wherein said RNAi construct is shown in FIG. 6.

8. The method of claim 1, wherein said visible reporter gene is green fluorescent protein (GFP) and said selectable marker gene is bar.

9. The method of claim 2, wherein said visible reporter gene is green fluorescent protein (GFP) and said selectable marker is bar.

* * * * *